(12) United States Patent
Barras et al.

(10) Patent No.: US 7,169,381 B2
(45) Date of Patent: Jan. 30, 2007

(54) COLON CLEANSING COMPOSITIONS AND METHODS

(75) Inventors: Norman Barras, Chilton (GB); Ian David Cox, Bilester (GB)

(73) Assignee: Norgine Europe BV, Amsterdam (NL)

( * ) Notice: Subject to any disclaimer, the term of this patent is extended or adjusted under 35 U.S.C. 154(b) by 313 days.

(21) Appl. No.: 10/693,328

(22) Filed: Oct. 24, 2003

(65) Prior Publication Data
US 2004/0143005 A1 Jul. 22, 2004

(30) Foreign Application Priority Data
Oct. 25, 2002 (GB) ................................. 0224909.2

(51) Int. Cl.
*A61K 31/74* (2006.01)
(52) U.S. Cl. ................................................. 424/78.01
(58) Field of Classification Search .................... None
See application file for complete search history.

(56) References Cited

U.S. PATENT DOCUMENTS

| | | | |
|---|---|---|---|
| 5,077,048 A | 12/1991 | Kimura et al. | ............... 424/422 |
| 5,274,001 A | 12/1993 | Borody | ......................... 514/474 |
| 5,458,890 A * | 10/1995 | Williford et al. | |
| 6,048,901 A | 4/2000 | Cleveland et al. | .......... 514/723 |
| 6,946,149 B2 | 9/2005 | Cleveland | |

FOREIGN PATENT DOCUMENTS

| | | |
|---|---|---|
| EP | 0 436 061 B1 | 5/1993 |
| EP | 0 397 689 B1 | 5/1994 |
| WO | WO 87/00754 | 2/1987 |
| WO | WO 89/05659 | 6/1989 |
| WO | WO 03/037298 A2 | 5/2003 |

OTHER PUBLICATIONS

"Magnesium Sulfate". Stedman's Medical Dictionary (Twenty-Second Edition). Williams and Wilkins Company, 1972. p. 737.*
"Sodium Ascorbate". Monograph 8723. The Merck Index (Twelfth Edition). Merck & Co., Inc. p. 1471.*
"Structure Activity Relationship and Drug Design". Remington's Pharmaceutical Sciences (Sixteenth Edition). Mack Publishing, 1980. pp. 420-425.*
Andorsky et al., "Colonic Lavage Solution (Polyethylene Glycol Electrolyte Lavage Solution) as a Treatment for Chronic Constipation: A Double-Blind, Placebo-Controlled Study," *Am. J. Gastroenterol.*, 85(3):261-265, 1990.
Braintree Laboratories, GoLYTELY®, product information, Jun. 5, 2002.
Braintree Laboratories, NuLYTELY®, product information, Jun. 5, 2002.
Clarkston et al., "Oral Sodium Phosphate Versus Sulfate-Free Polyethylene Glycol Electrolyte Lavage Solution in Outpatient Preparation for Colonoscopy: A Prospective Comparison," *Gastrointestinal Endoscopy*, 43(1):42-49, 1996.
Davis et al., "Development of a Lavage Solution Associated with Minimal Water and Electrolyte Absorption of Secretion," *Gastroenterology*, 78(5):991-995, 1980.
Evesa, Neohesperidine Dihydrochaleone (NHDC), product information, Oct. 24, 2002.
FLEET Company, Fleet Phospho-soda, Prescribing information—Oral Saline Laxative, Jul. 29, 2002.
Fordtran et al., "A Low-Sodium Solution for Gastrointestinal Lavage," *Gastroenterology*, 98:11-16, 1990.
Hammer et al., "Studies of Osmotic Diarrhea Induced in Normal Subjects by Ingestion of Polyethylene Glycol and Lactulose," *J. Clin. Invest.*, 84:1056-1062, 1989.
Ingebo and Heyman, "Polyethylene Glycol-Electrolyte Solution for Intestinal Clearance in Children with Refractory Encopresis," *Am. J. Dis. Child*, 142:340-342, 1988.
Klean-Prep; Abstract 35 075, with translation.
LinTech, Contract Food Laboratory Service, Jul. 31, 2002.
Merolli, "Flavor Enhancement: Taking a Closer Look," *Food Product Design*, Feb. 1997.
Movicol, Australian product information, Health Answers Australia Jul. 29, 2002.
Poon et al., "Two Liters of Polyethylene Glycol-Electrolyte Lavage Solution Versus Sodium Phosphate as Bowel Cleansing Regiment for Colonoscopy: A Prospective Randomized Controlled Trial," *Endoscopy*, 23(7):560-563, 2002.
Puxty and Fox, "Golytely: A new Approach to Faecal Impaction in Old Age", *Age and Aging*, 15:182-184, 1986.
Regev et al., "Comparison of Two Bowel Preparations for Colonscopy: Sodium Picosulphate with Magnesium Citrate Versus Sulphate-Free Polyethylene Glycol Lavage Solution," *Am. J. Gastroenterol.*, 93(9): 1478-1482, 1998.
Telstra, GLYCOPREP-C, Australian product information, Health Answers Australia, Jun. 5, 2002.
Thomas et al., "Patient Acceptance and Effectiveness of a Balanced Lavage Solution (Golytely) Versus the Standard Preparation for Colonoscopy," *Gastroenterology*, 82:435-437, 1982.
Tolia, "Use of a Balanced Lavage Solution in the Treatment of Fecal Impaction," *J. Pediatr. Gastroenterol. Nutr.*, 7(2):299-301, 1988.
Ungerer & Company Manufactures of Fragrances, Flavor, Essential Oils, Aroma Chemicals, and Oleore, Jul. 31, 2002.

* cited by examiner

*Primary Examiner*—Ardin H. Marschel
*Assistant Examiner*—Leslie Royds
(74) *Attorney, Agent, or Firm*—Yankwich & Associates, P.C.; Leon R. Yankwich; Michael R. Wesolowski

(57) ABSTRACT

A composition comprising, per liter of aqueous solution, from 30 to 350 g polyethylene glycol, from 3 to 20 g of an ascorbic acid component selected form the group consisting of ascorbic acid, a salt of ascorbic acid, or a mixture thereof, an alkali metal or alkaline earth metal sulphate, preferably from 1 to 15 g thereof, and optionally one or more electrolytes selected from sodium chloride, potassium chloride, and sodium hydrogen carbonate, and preferably also comprising flavorings, is effective in cleansing the gut in preparation for a endoscopy, especially colonoscopy. It is safer than conventional sodium phosphate-based gut cleansing compositions, and hence can be used for patients who would be at risk with sodium phosphate-based compositions, and is better tolerated than conventional PEG-based compositions, leading to better patient compliance and enabling effective out-patient use.

40 Claims, No Drawings

COLON CLEANSING COMPOSITIONS AND METHODS

The present application claims priority to co-pending British application number GB 0224909.2, filed Oct. 25, 2002, the disclosure of which application is specifically incorporated herein by reference without disclaimer.

1. Field of the Invention

The present invention relates to orthostatic lavage solutions, colon evacuants or colon cleansing compositions, also known as lavage compositions for cleansing the gastrointestinal tract, and methods of use of such compositions.

2. General Background

Colon cleansing is important prior to numerous diagnostic and surgical procedures, for example before colonoscopy, barium enema examination or colon surgery. It is also useful for preventing infection after surgery on the lower intestine. Colon cleansing is also known as colon clearing.

A variety of methods for colon cleansing are known. Dietary manipulation, laxatives, cathartics and enemas were traditionally used (Thomas, G. et al., *Gastroenterology*, 1982, 82, 435–437). Sodium phosphate solutions (Clarkston, W. K. et al., *Gastrointestinal Endoscopy*, 1996, 43, 43–48) and magnesium citrate/sodium picosulphate solutions (Regev, A. et al., *Am. J. Gastroenterol.*, 1998, 93, 1478–1482) have also been used.

Those methods suffer from various drawbacks. Dietary manipulation and laxatives are time consuming; enemas are unpleasant for the patient; and dangerous salt and water losses may occur with cathartics, enemas and with sodium phosphate solutions.

Sodium phosphate solutions, such as that available from C.B. Fleet Company Inc. (4615 Murray Place, PO Box 11349, Lynchburg, Va. 24506, USA) under the trade name Phospho-soda® are hyperosmotic solutions which increase retention of water in the intestine and thereby promote bowel movement. Phospho-soda comprises, per 5 ml portion, 2.4 g monobasic sodium phosphate monohydrate with 0.9 g dibasic sodium phosphate heptahydrate in a buffered aqueous solution. Typically 20 to 45 ml are taken by an adult patient followed by a large quantity of water. If the water is not taken, elevated serum sodium and phosphate levels may result, leading to serious kidney problems. The risk of those side effects makes it necessary for there to be direct medical supervision during administration of Phospho-soda.

Another approach to colon cleansing is orthostatic intestinal lavage, in which a large volume of an electrolyte solution is ingested, either by drinking or by infusion through a nasogastric tube. Such lavage solutions are also known as bowel lavage solutions. Consumption of the solution results in volume-induced diarrhoea and thus cleansing of the colon. The method is generally faster than the traditional approaches. The main component of early lavage solutions was sodium chloride. However, as a significant percentage of such saline-based lavage solutions is absorbed into the bloodstream in the gut of the patient, a rapid increase in intravascular volume results, which has caused serious complications in some patients.

In 1980, Davis and co-workers reported the development of a lavage solution, that they described as being associated with minimal water and electrolyte absorption or secretion (Davis G. R. et al., Gastroenterology, 1980, 78, 991–995). The solution included sodium sulphate and polyethylene glycol. Sulphate ions are poorly absorbed in the gut. As a result, sodium absorption is markedly reduced when sulphate, rather than chloride or bicarbonate, is the predominant counter-anion present in a lavage solution in the gut. In addition to sodium sulphate (40.0 mM, 5.68 g/l), the solution described by Davis et al. comprises sodium chloride (25 mM, 1.463 g/l), potassium chloride (10 mM, 0.745 g/l), sodium bicarbonate (20 mM, 1.680 g/l), polyethylene glycol (PEG 4000 "carbowax", 64 g/l) and water. The solution was administered in a quantity of 4 liters. The solution was shown to be effective in cleansing the gastrointestinal tract and it has been commercialised under the trade name GoLYTELY® (Braintree Laboratories Inc, Braintree, Mass., U.S.A.). The commercially available GoLYTELY composition, also known as Klean Prep®, as available after August 1996 and at the time of filing, is supplied in dry powder form comprising sodium sulphate (40.0 mM, 5.685 g/l), sodium chloride (25 mM, 1.464 g/l), potassium chloride (10 mM, 0.743 g/l), sodium bicarbonate (20 mM, 1.685 g/l) and PEG 3350 polyethylene glycol (59 g/l) for making up to 4 liters. GoLYTELY is also supplied in aqueous solution.

The GoLYTELY solution, whilst effective, has a very salty taste, which adversely affects patient compliance. Typically the composition is presented as four or more liters of aqueous solution, and it is important that the whole prescribed volume is consumed. Consumption of such large volumes of fluid can also affect compliance adversely.

Fordtran et al. (WO87/00754) subsequently developed a reduced sodium sulphate solution (RSS) comprising no sodium sulphate but instead having a relatively high concentration of polyethylene glycol (75 to 300 g/l). The preferred solution disclosed in WO87/00754 comprises PEG 3350 (120 g/l), sodium bicarbonate (1.68 g/l), potassium chloride (0.74 g/l) and sodium chloride (1.46 g/l) and it is also administered in a quantity of 4 liters. A solution very similar to the preferred solution of WO87/00754 is commercialised by Braintree Laboratories Inc (Braintree, Mass., U.S.A.) under the name NuLYTELY® (initially also under the name GoLYTELY-RSS). The NuLYTELY composition comprises PEG 3350 (105 g/l), sodium bicarbonate (1.43 g/l), potassium chloride (0.37 g/l) and sodium chloride (2.80 g/l) and it is supplied in dry powder form for making up to 4 liters.

Whilst being effective in colon cleansing in the clinic, both the GoLYTELY and the NuLYTELY solutions must be ingested in large quantities, typically four liters. Ingestion of such volumes of gut lavage solution is generally physically unpleasant or even impossible for many patients, may result in retching, and is time consuming. In spite of the absence of sodium sulphate in NuLYTELY, both NuLYTELY and GoLYTELY have an unpleasant salty taste. The unpleasant taste exacerbates the problem of patient compliance, particularly when the patient is not under medical supervision.

In WO 89/05659 (Borody) there is described an orthostatic lavage solution comprising polyethylene glycol, electrolytes and from 0.25 to 50 g/l ascorbic acid (vitamin C) or a salt thereof. The presence of ascorbic acid or a salt thereof is said to reduce the required volume of solution to 3 liters or less. Whilst about 3 g of ascorbic acid may be absorbed in the intestine (Hornig, D. et al., Int. J. Vit. Nutr. Res., 1980, 50, 309) any further ascorbic acid is reported in WO 89/05659 to contribute to the diarrhoea and to inhibit bacterial gas generation and bacterial reproduction. The ascorbic acid is also said to facilitate ingestion of the lavage solution because its pleasant acidic taste masks the usual nauseating taste of the salty polyethylene glycol solution.

The solutions described by Borody comprise polyethylene glycol (preferably PEG 3350 or PEG 4000) at a concentration of 30–60 g/liter together with inorganic electrolytes (sodium chloride, potassium chloride, sodium hydrogen carbonate and sodium sulfate). In any given solution, the quantity of PEG is described as being adjusted such that the osmolarity of the solution is approximately 289 mOsmol/kg (i.e. isotonic). The osmolarity of a solution may be measured using conventional laboratory techniques. It is also possible to calculate osmolarity from a knowledge of the components of a solution. Details of osmolarity calculations are given herein below.

A formulation as described by Borody has been available on the market in Australia for more than 10 years under the tradename GLYCOPREP C (Pharmatel). The GLYCOPREP C dry composition comprises PEG 3350 (53 g/l), sodium chloride (2.63 g/l), potassium chloride (0.743 g/l), sodium sulphate (5.6 g/l), ascorbic acid (6 g/l), aspartame (0.360 g/l), citric acid (0.900 g/l) and lemon flavour (0.090 g/l). 3 liters of the solution are generally administered.

Whilst the addition of ascorbic acid goes some way towards providing an improved bowel preparation, that preparation must be ingested in quantities of approximately 3 liters. Ingestion of such volumes of gut lavage solution is still generally physically unpleasant or, for some patients, even impossible, may result in retching, and is time consuming. Accordingly there remains a requirement for lavage solutions with a more pleasant taste that are effective in a smaller volume.

Colon clearance is important before numerous surgical or diagnostic procedures, including colonoscopy, barium enema examination, sigmoidoscopy and colon surgery. It is desirable that the colon clearance may be carried out by the patient himself or herself without medical supervision at home in advance of attending the hospital or surgery where the surgical or diagnostic procedure is to take place. It is important that patient compliance is good without medical supervision if satisfactory colon clearance is to be achieved.

The compositions of the prior art are summarised in Table 1. In that table, the indicated quantities are the quantities present per liter of aqueous solution. The calculated osmolarity of the solutions (in mOsmol/kg) is also given in the table together with the recommended dose (in liters).

ascorbic acid and/or one or more salts thereof, a relatively high concentration of PEG and, optionally, further electrolytes, has a powerful cleansing or purging action. Hence it has been found that smaller volumes of solution are needed and yet the solution remains palatable. The cleansing solution achieves satisfactory colon cleansing for, e.g. colonoscopy, when used in a quantity of approximately 2 liters.

The invention provides a dry composition for admixture with water wherein the dry composition comprises, per liter of aqueous solution to be made, the following components:
   a) 80 to 350 g of a polyethylene glycol;
   b) 3 to 20 g of ascorbic acid, one or more salts of ascorbic acid or a mixture of ascorbic acid and one or more salts of ascorbic acid;
   c) 1 to 15 g of an alkali metal or alkaline earth metal sulphate or a mixture of alkali metal or alkaline earth metal sulphates; and
   d) optionally one or more electrolytes selected from sodium chloride, potassium chloride and sodium hydrogen carbonate;

the components of the composition being selected such that an aqueous solution made up to 1 liter has an osmolarity within the range of from 300 to 700 mOsmol/kg.

The invention also provides a cleansing solution comprising an aqueous solution of the dry composition of the invention, the components having the concentrations stated above, the composition having an osmolarity within the range defined above, and the volume of the composition being from 0.51 to 51.

The solutions of the invention are not isotonic i.e. they do not have the same osmotic pressure as the blood in the gut vasculature. The solutions are, however, approximately iso-osmolar, that is to say, the solution excreted from the patient has substantially the same ion content as the solution ingested. Consequently, there is no substantial net change in the ion levels in the blood of the patient.

TABLE 1

Composition of prior art colon cleansing treatments

| Formulation | PEG g | $Na_2SO_4$ g | $NaHCO_3$ g | NaCl g | KCl g | Vit C g | Osm | Vol l |
|---|---|---|---|---|---|---|---|---|
| GoLYTELY | 60 | 5.7 | 1.93 | 1.46 | 0.75 | — | 255 | 4 |
| NuLYTELY | 105 | — | 1.43 | 2.8 | 0.37 | — | 176 | 4 |
| Glycoprep C | 53 | 5.6 | — | 2.63 | 0.74 | 6.0 | 291 | 3 |

DESCRIPTION OF THE INVENTION

It has now been found, surprisingly, that a cleansing solution comprising an alkali metal or alkaline earth metal sulphate, ascorbic acid and/or one or more salts thereof, a relatively high concentration of PEG and, optionally, further electrolytes, has a cleansing action that is effective when administered in a small volume, and is palatable. The cleansing solution comprising a composition of the invention achieves satisfactory colon cleansing when used in a quantity of approximately 2 liters. Conventional cleansing solutions must be used in a quantity of at least 3 to 4 liters.

PEG has been known to contribute towards the diarrhoea-producing effect of PEG-containing solutions by promoting malabsorption of electrolytes. However, it has now been found, surprisingly, that a cleansing solution which comprises an alkali metal or alkaline earth metal sulphate, The osmolarity of a solution is the number of non-permeating particles dissolved in a solution. For a substance that remains completely associated as a unit in solution (e.g. a neutral organic molecule) the osmolarity and the molarity of a solution are essentially the same. For a substance that dissociates when it dissolves (e.g. an ionic salt), the osmolarity is the number of moles of individual dissolved species in solution after dissolution.

The osmolarity of a solution can be measured using standard laboratory techniques. It can also be calculated from a knowledge of the components of a solution. As an example, the osmolarity of the GoLytely solution may be calculated as follows:

PEG: 60 g, MW=3350, one species per mole in solution:

Contribution=60/3350*1=18.0 mOsmol/kg $Na_2SO_4$: 5.7 g, MW=142, three species per mole in solution:

Contribution=5.7/142*3=120.4 mOsmol/kg

NaHCO$_3$: 1.93 g, MW=84, two species per mole in solution:

Contribution=1.93/84*2=46.0 mOsmol/kg

NaCl: 1.46 g, MW=58.5, two species per mole in solution:

Contribution=1.46/58.5*2=50.0 mOsmol/kg

KCl: 0.75 g, MW=74.5, two species per mole in solution:

Contribution=0.75/74.5*2=20.1 mOsmol

Total Osmolarity=255 mOsmol/kg

In some cases, a calculated osmolarity disagrees with a measured osmolarity. There are a variety of possible reasons for that, mostly connected with the fact that the number of free dissolved species in solution may not be exactly that assumed from ideal behaviour. For example, if several components are present, those may aggregate and lead to the number of independent dissolved species being lower than that calculated. As a further example, in dependence on the pH of the solution, organic acids and bases can be incompletely dissociated or associated.

A cleansing solution comprising PEG at a concentration of over 100 g/l has been described previously (NuLYTELY). It has generally been assumed that cleansing solutions must be isotonic, i.e. have the same osmolarity as the vascular fluid in the gut. The high concentration of PEG was thus accompanied by a low concentration of electrolyte salts so that the cleansing solution was isotonic. For example, sodium sulfate is omitted from the NuLYTELY solution. It has now been found, surprisingly, that it is not necessary for the cleansing solution to be isotonic and, furthermore, that a hypertonic solution comprising PEG, an alkali metal or alkaline earth metal sulphate or a mixture of alkali metal or alkaline earth metal sulphates, electrolytes and ascorbic acid and/or one or more salts thereof is a cleansing solution that is more effective than isotonic solutions of the prior art.

In healthy volunteers, at an administered volume of 2 liters, a hypertonic cleansing solution of the present invention has been found to cause a 50% increase in stool weight and stool volume output compared with an isotonic solution lacking sodium-sulphate and ascorbic acid but otherwise having the same composition, that is to say, the same concentrations of PEG, sodium bicarbonate, sodium chloride and potassium chloride. No adverse side effects were observed. The hypertonic cleansing solution of the invention was also found to be more effective at that administered volume than prior art compositions that are isotonic and comprise a lower concentration of sodium sulphate.

Preferably the osmolarity of a cleansing solution of the present invention is 330 mOsmol/kg or greater, more preferably 350 mOsmol/kg or greater, still more preferably 400 mOsmol/kg or greater, for example 460 mOsmol/kg or greater. Preferably, the osmolarity of the cleansing solution of the present invention is 600 mOsmol/kg or lower, more preferably 550 mOsmol/kg or lower, still more preferably 500 mOsmol/kg or lower, for example 470 mOsmol/kg or lower. For example the osmolarity may be in a range wherein the lower limit is selected from any of 330, 350, 400 and 460 mOsmol/kg, and the upper limit is selected, independently, from any of 600, 550, 500 and 470 mOsmol/kg.

Whereas previously it was thought to be necessary for a cleansing solution to be isosmolar, and pains were taken to adjust them to be so, it has now, surprisingly, been found that high osmolarity is not only safe, but more effective than prior art solutions and that patients are less likely to vomit with the lower volume of ingested fluid. When the osmolarity is contributed to by the PEG, the double effect of high PEG concentration and increased osmolarity drives the cleansing solution at a higher pace with reduced side effects and yet with greater safety. From the resulting effluent volume measurements we have found that the combination of the two effects is synergistic.

The polyethylene glycol (PEG) used in a composition of the present invention preferably has an average molecular weight of 2000 or greater. Preferably the PEG has an average molecular weight of 2500 or greater. Preferably the PEG has an average molecular weight of 4500 or lower. For example the PEG may be PEG 3350 or PEG 4000. Optionally, the PEG used in a composition of the invention may comprise two or more different PEG species. A composition of the invention preferably comprises 90 g or more of PEG per liter, more preferably 100 g or more of PEG per liter. Preferably, a composition of the invention comprises 250 g or less of PEG per liter, more preferably 150 g or less of PEG per liter, still more preferably 140 g or less of PEG per liter, still more preferably 125 g or less of PEG per liter. For example, a composition of the present invention may comprises PEG at a concentration within a range wherein the lower limit is 90 or 100 g per liter and the upper limit is, independently, 350, 250, 150 or 125 g per liter. For example, a composition of the invention may comprise 100 or 125 g per liter. Most preferably a composition of the invention comprises 100 g of PEG per liter.

Preferably the alkali metal or alkaline earth metal sulphate or the mixture of alkali metal or alkaline earth metal sulphates is present in a cleansing composition of the invention in a quantity of 2 g or more per liter, more preferably in a quantity of 3 g or more per liter, still more preferably in a quantity of 5 g or more per liter. Preferably the alkali metal or alkaline earth metal sulphate or the mixture of alkali metal or alkaline earth metal sulphates is present in the cleansing compositions of the invention in a quantity of 10 g or less per liter, more preferably in a quantity of 9 g or less per liter, still more preferably in a quantity of 7.5 g or less per liter. For example, the alkali metal or alkaline earth metal sulphate or the mixture of alkali metal or alkaline earth metal sulphates may be present in a quantity within a range in which the lower limit is selected from any of 2, 3 and 5 g per liter and the upper limit is selected, independently, from any of 10, 9 and 7.5 g per liter. For example the alkali metal or alkaline earth metal sulphate or the mixture of alkali metal or alkaline earth metal sulphates is present in a quantity of 5 g or 7.5 g per liter, most preferably 7.5 g per liter.

The alkali earth metal or alkaline earth metal may be, for example, sodium, magnesium or calcium. Sodium is generally preferred, but magnesium or calcium may be used.

A composition of the invention preferably comprises sodium chloride. Sodium chloride is preferably present in a quantity of 0.5 g or more per liter, more preferably 1 g or more per liter, still more preferably a quantity of 2 g or more per liter. Sodium chloride is preferably present in a quantity of 7 g or less per liter, more preferably 5 g or less per liter, still more preferably a quantity of 4 g or less per liter. For example, sodium chloride may be present in at a concentration within a range in which the lower limit is selected from any of 0.5, 1 and 2 g per liter and the upper limit is selected, independently, from any of 7, 5 and 4 g per liter.

A composition of the invention preferably comprises potassium chloride. Preferably potassium chloride is present in a quantity of 0.2 g or more per liter, more preferably in a quantity of 0.5 g or more per liter, most preferably in a quantity of 0.7 g or more per liter. Preferably potassium chloride is present in a quantity of 4 g or less per liter, more preferably in a quantity of 2 g or less per liter, most preferably in a quantity of 1.3 g or less per liter. For example, potassium chloride may be present in at a concentration within a range in which the lower limit is selected from any of 0.2, 0.5 and 0.7 g per liter and the upper limit is selected, independently, from any of 4, 2, and 1.3 g per liter.

A composition of the invention may comprise sodium bicarbonate. Because of the reaction between sodium bicarbonate and acids, bicarbonate ions are generally destroyed, with accompanying effervescence as $CO_2$ is produced, on addition of water to a composition comprising ascorbic acid and a bicarbonate. The same reaction may occur in a dry powder composition if small amounts of moisture, for example atmospheric moisture, are present. The reaction between bicarbonate and ascorbic acid in the dry powder composition may be avoided if coated ascorbic acid is used. The reaction may also be avoided by packaging the dry composition in two separate individual units such that the bicarbonate and the ascorbic acid are not in contact.

The term "ascorbate component" is used herein to denote the ascorbic acid, one or more salts thereof or a mixture of ascorbic acid that is used in a composition of the present invention. The ascorbate component is present in a composition of the invention in a quantity of from 3–20 g per liter of solution. Preferably the ascorbate component is present in a quantity of 4 g or more per liter, more preferably in a quantity of 5 g or more per liter. Preferably the ascorbate component is present in a quantity of 15 g or less per liter, more preferably in a quantity of 10 g or less per liter. For example, the ascorbate component may be present in a quantity within a range in which the lower limit is 4 or 5 g per liter and the upper limit is, independently, 15 or 10 g per liter. For example, the ascorbate component is present in a quantity of 5 to 10 g per liter, for example, 5 or 10 g per liter.

Preferred salts of ascorbic acid are alkali metal and alkaline earth metal salts, for example sodium ascorbate, potassium ascorbate, magnesium ascorbate and calcium ascorbate. A particularly preferred salt of ascorbic acid is sodium ascorbate. Preferably the ascorbate component comprises both ascorbic acid and one or more salts thereof. Preferably the ascorbic acid and the salt(s) thereof are present in a weight ratio within the range of from 1:9 to 9:1. Ascorbic acid and salts thereof may, in practice, be provided as hydrates. If a hydrate is used, the weight and/or weight ratio mentioned here is the weight and/or weight ratio of ascorbic acid or salt(s) thereof without water of hydration. Preferably the ascorbic acid and the salt(s) thereof are present in a weight ratio within the range of from 2:8 to 8:2, more preferably 3:7 to 7:3, still more preferably 4:6 to 6:4, for example 4.7 to 5.9.

It has been found previously by others that the plasma bicarbonate ion level may fall following use of cleansing solutions based on 0.9% saline or 7.2% mannitol that do not contain a balanced amount of bicarbonate. A lowered plasma bicarbonate level may have serious adverse clinical consequences associated with a reduced blood pH (acidosis) and consequent reduced capacity to transport $CO_2$ in the bloodstream. Acidosis may lead to weakness, disorientation, coma and eventually death. However, it has now been found according to the present invention that plasma bicarbonate lowering is much reduced by the use of a composition comprising both ascorbic acid and one or more salts thereof. The presence of an ascorbate salt contributes to the osmotic load of the solution and also aids the maintenance of the bicarbonate level. This is a further advantage of the compositions of the present invention.

Compositions of the invention are preferably flavoured. Flavouring for use in compositions of the invention should preferably mask saltiness, be relatively sweet but not excessively so, and be stable in the composition. Flavouring makes the solutions more palatable and thus aids patient compliance. Preferred flavorings include lemon e.g. Ungerer Lemon (available from Ungerer Limited, Sealand Road, Chester, England CH1 4LP) strawberry e.g. Ungerer Strawberry, grapefruit e.g. Ungerer Grapefruit flavouring powder, blackcurrant e.g. Ungerer Blackcurrant, pineapple e.g. IFF (International Flavours and Fragrances) Pineapple flavouring powder and vanilla/lemon and lime e.g. IFF Vanilla and Givaudin Roure Lemon and Lime Flav-o-lok. Those and further suitable flavorings are available from International Flavors and Fragrances Inc. (Duddery Hill, Haverhill, Suffolk, CB9 8LG, England), Ungerer & Company (Sealand Road, Chester, England CH1 4LP) or Firmenich (Firmenich UK Ltd., Hayes Road, Southall, Middlesex UB2 5NN). More preferred flavorings are lemon, kiwi, strawberry and grapefruit. The most preferred flavouring is lemon.

Preferably compositions of the invention comprise a sweetener. Sugar-based sweeteners are not suitable because delivery of unabsorbed sugars to the colon provides a substrate for bacteria. Such sugars may be metabolised by the bacteria to form explosive gases such as hydrogen and methane. The presence of explosive gases in the colon can be highly dangerous when electrical apparatus is to be used during colonoscopy or other procedures. Preferred sweeteners include aspartame, acesulfame K and saccharine or combinations thereof. Citric acid may also be present as a taste enhancer.

The ascorbic acid and/or salt(s) of ascorbic acid in a dry composition of the present invention may be coated. A coating helps to maintain the stability of the ascorbic acid and/or the salt(s) thereof. As stated above, ascorbic acid and salts thereof are otherwise poorly stable in the presence of moisture.

A dry composition in accordance with the invention may be in powder, granular or any other suitable physical form. A dry composition of the invention may be provided in unit dosage form, for example, in a sachet. Preferably a dry composition is provided in two or more component form, in which the ascorbic acid and/or salt(s) thereof are packaged separately from other components. For example, a first component, for example, in a unit dose form, for example, a sachet may contain polyethylene glycol, sodium sulphate, sodium chloride, potassium chloride, sweetening and flavouring agents, and a second component, for example, a unit dose form, for example, a sachet containing ascorbic acid and sodium ascorbate.

A composition of the invention may be provided as a solution in water, for example, in one or more containers, each containing, for example, 0.5 or 1 liter of solution.

The present invention also provides a method of cleansing the colon of a mammal, comprising administering orally to the mammal a cleansing fluid comprising, per liter, the following components:
  a) 80 to 350 g of a polyethylene glycol;
  b) 3 to 20 g of ascorbic acid, one or more salts of ascorbic acid or a mixture of ascorbic acid and one or more salts of ascorbic acid;
  c) 1 to 15 g of an alkali metal or alkaline earth metal sulphate or a mixture of alkali metal or alkaline earth metal sulphates; and
  d) optionally one or more electrolytes selected from sodium chloride, potassium chloride and sodium hydrogen carbonate;

the components of the composition being selected such that the cleansing fluid has an osmolarity within the range of from 300 to 700 mOsmol/kg, the volume of fluid administered being from 1.5 to 3 liters for an adult human and pro rata for a mammal other than an adult human.

The exact quantity of the solution of the invention to be administered will depend on the patient being treated. For example, a smaller volume of cleansing solution is appropriate in the treatment of small children and a higher volume of cleansing solution is appropriate in patients with prolonged colonic transit times.

The method of the present invention may be used to cleanse the colon prior to carrying out a diagnostic, therapeutic or surgical procedure on the colon, rectum or anus or elsewhere in the abdomen. The diagnostic or surgical procedure may, for example, be colonoscopy, barium enema examination, sigmoidoscopy or colon surgery.

The method of the present invention may also be used in the treatment of acute gastrointestinal infections, for example bacterial or viral gastroenteritis. The aim in such a treatment is to remove stools from the infected colon so that the patient absorbs fewer toxins and has a shorter period of diarrhoea, toxicity, anorexia, nausea or vomiting. Upon developing diarrhoea, cramping and malaise the use of the purgative product removes from the bowel the offending, infected column of bowel flora, so ameliorating the infection in a short length of time.

Preferably, the total volume of solution is administered over 1 to 4 hours. The 1 to 4 hours may be in a continuous period or a discontinuous period. In discontinuous administration, a portion of the solution, typically approximately half, may be administered the evening before the diagnostic, therapeutic or surgical procedure is to be carried out, with the remainder of the solution being administered on the day of the procedure.

A composition for use in a method of the invention has the preferred features described above in respect of the composition of the invention.

The invention further provides a dry composition for admixture with water wherein the dry composition comprises, per liter of aqueous solution to be made, the following components:

30 to 350 g of a polyethylene glycol
   3 to 20 g of ascorbic acid and one or more salts of ascorbic acid
   optionally one or more electrolytes selected from sodium chloride, potassium chloride, sodium hydrogen carbonate and the alkali metal or alkaline earth metal sulphates.

The invention also provides a solution of the above dry composition.

It has been found, surprisingly, that a colon cleansing solution comprising ascorbic acid and one or more salts of ascorbic acid has fewer side effects than a cleansing solution comprising ascorbic acid and no salts thereof. Furthermore, a colon cleansing solution comprising ascorbic acid and one or more salts of ascorbic acid has been found to be even more efficacious in its colon cleansing action than a solution comprising ascorbic acid and no salts thereof. Cleansing solutions comprising a salt of ascorbic acid but no ascorbic acid have also been found to be less efficacious than solutions comprising both ascorbic acid and one or more salts thereof.

The levels of plasma bicarbonate and other anion may fall during use of cleansing solutions comprising ascorbic acid alone. The presence of one or more salts of ascorbic acid contribute to the osmotic load of the solution and also aid the maintenance of the plasma bicarbonate level. The fall in the level of plasma bicarbonate is much reduced by the use of a composition comprising both ascorbic acid and one or more salts thereof.

Any suitable salt of ascorbic acid may be used. Preferred salts of ascorbic acid are alkali metal and alkaline earth metal salts, for example sodium ascorbate, potassium ascorbate, magnesium ascorbate and calcium ascorbate. A particularly preferred salt of ascorbic acid is sodium ascorbate. Preferably, the salt is sodium ascorbate.

Preferably the ascorbic acid and the salt(s) thereof are present in a weight ratio in the range of from 1:9 to 9:1. Ascorbic acid or salts thereof may, in practice, be provided as hydrates. If a hydrate is used, the weight and/or weight ratio mentioned herein is the weight and/or weight ratio of the ascorbic acid and the salt thereof without water of hydration. Preferably the ascorbic acid and the salt thereof are present in a weight ratio in the range of 2:8 to 8:2, more preferably 3:7 to 7:3, still more preferably 4:6 to 6:4, for example 4.7:5.9.

Preferably, a composition of the invention comprising ascorbic acid and one or more salts thereof further comprises one or more electrolytes selected from sodium chloride, potassium chloride, sodium hydrogen carbonate and sodium sulphate. Preferably, a composition of the invention comprises sodium sulphate.

A composition of the invention as described above may be provided as a solution in water or as a dry composition for making up into a solution. In such a dry formulation, the ascorbic acid and/or the salt(s) of ascorbic acid may be coated. Such a coating helps to maintain stability of ascorbic acid or salt(s) thereof. Ascorbic acid and salts thereof are otherwise poorly stable in the presence of moisture.

A dry composition may be provided in a unit dosage form, for example, in a sachet. A dry composition may be provided in two or more component form, in which the ascorbic acid and/or the salts thereof are packaged separately from other components. For example, a first unit dosage form, for example, a first sachet may contain polyethylene glycol, sodium sulphate, sodium chloride, potassium chloride, sweetening and flavouring and a second unit dosage form, for example, a second sachet may contain ascorbic acid and sodium ascorbate.

The present invention further provides a method of cleansing the colon of a mammal, comprising administering orally to the mammal a preparation comprising, per liter the following components:

30 to 350 g polyethylene glycol
   3 to 20 g of a mixture of ascorbic acid and a salt of ascorbic acid
   optionally one or more electrolytes selected from sodium chloride, potassium chloride, sodium hydrogen carbonate and the alkali metal or alkaline earth metal sulphates, the volume of composition administered being from 1.5 to 4 liters for an adult human and pro rata for a mammal other than an adult human. The exact quantity of solution to be administered will depend on the patient being treated. For example, a smaller dose of cleansing solution is appropriate in the treatment of small children and a higher dose of cleansing solution is appropriate in patients with prolonged colonic transit times.

A method of the present invention may be used to cleanse the colon prior to carrying out a diagnostic, therapeutic or surgical procedure on the colon, rectum or anus or elsewhere in the abdomen. A diagnostic or surgical procedure may, for example, be colonoscopy, barium enema examination, sigmoidoscopy or colon surgery. The method of the present invention may also be used in the treatment of acute gastrointestinal infections, for example bacterial or viral gastroenteritis.

Preferably, the total volume of fluid is administered over 1 to 4 hours. The 1 to 4 hours may be in a continuous period or may be in a discontinuous period. In one mode of administration, a portion of the solution, typically approximately half, may be administered the evening before the diagnostic, therapeutic or surgical procedure is to be carried out, with the remainder of the solution being administered on the day of the procedure.

An ascorbic acid and ascorbic acid salt-containing preparation for use in a method of the invention has the preferred features described above in respect of the corresponding ascorbic acid and ascorbic acid salt-containing preparation of the invention.

The present invention further provides the use of a PEG for the manufacture of a medicament for cleansing the colon of a mammal according to an administration regime comprising the consecutive steps of a) administering 0.5 to 3.0 liters of a colon cleansing solution comprising a PEG (volume $V_{PEG}$) over a period of time $t_1$ and b) administering 0.3 to 2.0 liters of clear fluid (volume $V_{cf}$) over a period of time $t_2$.

The invention also provides a method of cleansing the colon of a mammal, comprising administering orally to the mammal in consecutive steps:

a) 0.5 up to 3.0 liters of a cleansing solution comprising PEG (volume $V_{PEG}$) over a period of time $t_1$ and b) 0.3 up to 2.0 liters of clear fluid (volume $V_{cf}$) over a period of time $t_2$.

$t_1$ is preferably up to 2 hours, more preferably up to 1 hour 30 minutes, typically approximately one hour. $t_1$ is preferably greater than 15 minutes, more preferably greater than 30 minutes. Similarly, $t_2$ is preferably up to 2 hours, more preferably up to 1 hour 30 minutes, typically approximately one hour. $t_2$ is preferably greater than 15 minutes, more preferably greater than 30 minutes.

Preferably, $V_{PEG}$ is 500 ml or greater, more preferably, $V_{PEG}$ is 800 ml or greater. Preferably, $V_{PEG}$ is 2000 ml or less, more preferably, $V_{PEG}$ is 1500 ml or less. For example $V_{PEG}$ is approximately 1000 ml. Preferably, $V_{cf}$ is 300 ml or greater, more preferably, 400 ml or greater. Preferably, $V_{cf}$ is 1500 ml or less, preferably 1000 ml or less. For example $V_{cf}$ is approximately 500 ml. In practice, under supervision in the clinic, clear fluid may be given until faecal output is clear and no longer contains any solid material.

Using the regime of the invention, it is found, surprisingly, that the weight of stool recovered is increased in comparison to a normal cleansing regime, in which only colon cleansing solution is administered. The invention hails the start of a new era in which use of hypertonic solutions comprising PEG, together with added electrolytes means that patients will have to drink added water to provide the orthostatic lavage power. The markedly reduced volume of the active solution required to be drunk may be followed by any fluid that the patient chooses, including water, lemonade and others.

It is postulated by the present inventors that the total ingested osmotic load is of importance in determining the success of the colon cleansing action. Using the regime of the invention, ingestion of the required osmotic load is possible in a shorter time period which makes the onset of the effect of the cleansing more rapid.

The use of a clear fluid enables the progress of the colon cleansing, including the end point, to be assessed by visual inspection of the faecal output. When the faecal output is clear, no further fluid need be ingested by the patient. The clear fluid may be any fluid that allows inspection of colonic output. Typically the clear fluid is a water-based beverage, including, for example, water, lemonade, cola drinks, cordial drinks, clear fruit juices and even clear alcohol-containing beverages, for example beer. It is desirable that the clear fluid does not contain substantial amounts of or essentially any dietary fibre, as such fibre interferes with the cleansing of the colon according to the present invention. Accordingly, fruit juices, for example orange juice and kiwi juice, and fruit "squashes" should be strained before use. Clear fruit cordials, for example, lime cordial, are generally suitable. In view of the desirability of avoiding drinks containing glucose, so as to reduce the risk of explosive concentrations of hydrogen or methane building up in the gut, "diet" drinks containing no or low sugar are especially suitable, for example liquid drinks for diabetics, diet Coke (RTM), diet lemonade, dietary carbonated drinks or dietary cordials.

In general, the larger the volume of cleansing solution that is administered, the greater the quantity of stools that is collected. As mentioned in the introduction in relation to the prior art, 4 liters of colon cleansing solution is generally administered over 3 to 4 hours. Colon cleansing solutions generally have an unpleasant taste and many patients have difficulty ingesting the large quantity of solution typically necessary. It has now been found according to a further aspect of the present invention that highly effective colon cleansing can be achieved by administering first a cleansing solution, the volume being less than the volume described in the prior art, followed by administration of a clear fluid.

Suitable colon cleansing solutions for use in the method include in particular the colon cleansing solutions of the present invention described above.

Patient compliance is improved because the volume of cleansing solution that must be ingested is smaller than in the prior art methods. In comparison with ingestion of a cleansing solution of volume ($V_{PEG}+V_{cf}$) but with the same total quantity of composition components, the effectiveness is, surprisingly, not reduced. Water alone is not active as a cleansing solution. It is normally simply absorbed in the gut.

Preferably, the colon is cleared prior to carrying out a diagnostic, therapeutic or surgical procedure on the colon, rectum or anus or elsewhere in the abdomen. The diagnostic or surgical procedure may, for example, be colonoscopy, barium enema examination, sigmoidoscopy or colon surgery.

As a variant of the two step aspect of the invention, there is provided the use of a PEG for the manufacture of a medicament for cleansing the colon of a patient according to an administration regime comprising the consecutive steps of:

a) administering 0.5 up to 3.0 liters of a first PEG-containing colon cleansing solution (volume $V_{PEG}$) over a period of time $t_1$.

b) administering 0.3 up to 2.0 liters of clear fluid (volume $V_{cf}$) over a period of time $t_2$, and c) administering 0.5 up to 3.0 liters of a second PEG-containing colon cleansing solution (volume $V2_{PEG}$) over a period of time $t_3$.

The present invention also provides a method for cleansing the colon of a patient according to an administration regime comprising the consecutive steps of:

a) administering 0.5 up to 3.0 liters of a first PEG-containing colon cleansing solution (volume $V_{PEG}$) over a period of time $t_1$.

b) administering 0.3 up to 2.0 liters of clear fluid (volume $V_{cf}$) over a period of time $t_2$, and c) administering 0.5 up to 3.0 liters of a second PEG-containing colon cleansing solution (volume $V2_{PEG}$) over a period of time $t_3$.

It is found that the effectiveness and the patient compliance is further increased when the colon cleansing solution is administered in two doses separated by ingestion of a volume of water, when compared with the administration of a single dose of total equal volume (i.e. $V_{PEG}+V2_{PEG}$).

Preferably, $V_{PEG}$ is 500 ml or greater, more preferably, $V_{PEG}$ is 800 ml or greater. Preferably, $V_{PEG}$ is 2000 ml or less, more preferably, $V_{PEG}$ is 1500 ml or less. For example $V_{PEG}$ is approximately 1000 ml. Preferably, $V2_{PEG}$ is 500 ml or greater, more preferably, $V2_{PEG}$ is 800 ml or greater. Preferably, $V2_{PEG}$ is 2000 ml or less, more preferably, $V2_{PEG}$ is 1500 ml or less. For example $V2_{PEG}$ is approximately 1000 ml. Preferably, $V_{cf}$ is 300 ml or greater, more preferably, 400 ml or greater. Preferably, $V_{cf}$ is 1500 ml or less, preferably 1000 ml or less. For example $V_{cf}$ is approximately 500 ml.

$t_1$ is preferably 15 minutes or greater, more preferably from 30 minutes or greater. $t_1$ is preferably 2 hours or less, more preferably 1 hour 30 minutes or less. Typically $t_1$ is approximately one hour. Similarly, $t_2$ is preferably 15 minutes or greater, more preferably from 30 minutes or greater. $t_2$ is preferably 2 hours or less, more preferably 1 hour 30 minutes or less. Typically $t_2$ is approximately one hour. $t_3$ is preferably 15 minutes or greater, more preferably 30 minutes or greater. $t_3$ is preferably 2 hours or less, more preferably 1 hour 30 minutes or less. Typically $t_3$ is approximately one hour.

Preferably, the administration of the second dose of colon cleansing solution is followed by a second dose of clear fluid ($V2_{cf}$) over a period of time $t_4$. Preferably, $V2_{cf}$ is 500 ml or greater, more preferably, 800 ml or greater. Preferably, $V2_{cf}$ is 2000 ml or less, preferably 1500 ml or less. For example $V2_{cf}$ is approximately 1000 ml. In practice, under supervision in the clinic, clear fluid may be given until faecal output is clear and no longer contains any solid material. $t_4$ is preferably 30 minutes or greater, more preferably 1 hour or greater. $t_4$ is preferably 3 hours or less, more preferably 2 hour 30 minutes or less. Typically $t_4$ is approximately two hours.

The volume of stools produced is significantly increased by the addition of steps in which clear fluid is administered in accordance with the invention. The acceptability of the treatment to the patient is much increased. Of nine volunteer subjects, eight preferred administration of the cleansing solution in two doses separated by a dose of water over administration of the cleansing solution in a single, larger dose.

Suitable colon cleansing compositions for use in the method of the invention include in particular the compositions of the invention described above.

A composition may be provided in two or more component form. For example, a first component may be a composition for making up a first PEG-containing colon cleansing, a second component being a composition for making up a second PEG-containing colon cleansing solution. Preferably, one or both of the components comprise(s) ascorbic acid and/or a salt thereof. The two components are preferably in unit dosage form, for example, comprising the composition in a sachet or other appropriate container. In such an arrangement, the ascorbic acid and/or the salts thereof are preferably packaged separately from other components. For example a first sachet may contain polyethylene glycol, sodium sulphate, sodium chloride, potassium chloride, sweetening and flavouring and a second sachet may contain ascorbic acid and sodium ascorbate, those sachets together being for making up the first colon cleansing solution. A third sachet maybe provided, containing polyethylene glycol, sodium sulphate, sodium chloride, potassium chloride, sweetening and flavouring and a fourth sachet containing ascorbic acid and sodium ascorbate, those sachets together being for making up the second colon cleansing solution.

The various two or more component systems for providing compositions of the invention generally comprise the relevant composition in unit dosage form. A unit dose is generally an amount of dry composition suitable for making up to a defined volume with water. The volume may be any suitable volume, for example, for use in a two step or multi-step regime as described above, each unit dose may be suitable for making the total volume of solution for use in one of the defined cleansing steps. Alternatively, a unit dose may be suitable for making up to a defined volume, for example, a liter of cleansing solution.

It is convenient for the patient to provide the dry composition in the form of a kit, for example, a box, comprising the composition and instructions for its use. The composition is preferably in the form of unit dose component(s) as described above.

The present invention also provides the use of a solution comprising ascorbic acid and/or one or more salts thereof, an alkali metal or alkaline earth metal sulphate, a relatively high concentration of PEG and, optionally, further electrolytes for the treatment of patients with constipation, intestinal gas, symptoms of recurrent cramping or anorectal irritation. The PEG is consumed at a dose of 200 g or more per day, preferably more than 200 g per day, preferably more than 300 g per day, in divided doses. It may be provided in solid form which may be dispersed in an aqueous medium and administered from 1 to 4 times per day, preferably from 1 to 2 times per day. The number of administrations per day depends on the severity of the constipation.

Phase III clinical trials comparing the efficacy, safety and patient acceptance of a composition of the present invention (NRL994) with a polyethylene glycol+electrolyte (PEG+E) composition Klean-Prep® (also known as GoLYTELY) and with a sodium phosphate solution (NaP, also known as FLEETS) demonstrate an efficacy equal to that of the PEG+E and the NaP compositions, see Example 6.

Furthermore, the composition of the invention was better accepted than PEG+E, which acceptance is related to the improved taste and lower volume to be taken. In addition, NRL994 was shown to be as safe as PEG+E in a patient group that is enhanced for risk factors (hospitalised patients). Moreover, the comparison with NaP indicated an improved safety profile for the composition of the invention without clinically significant electrolyte alterations or disturbances. Overall, the composition of the invention provides an effective and safe bowel cleansing procedure with patient compliance equivalent to that with NaP. Furthermore, the composition of the invention avoids the need to limit its use to younger and more healthy subjects undergoing a routine colonoscopy, as required by NaP.

Accordingly, a composition of the present invention may be used to treat patient populations for which PEG+E or especially, NaP, would be considered unsuitable or unsafe; for example, outpatients, young and old patients, and patients having clinical conditions that would make them unsuitable for treatment, especially with NaP.

EXAMPLES

Example 1

Comparison of Effectiveness of 2-Liter Solutions of Movicol, Movicol+Ascorbic Acid and Movicol+Ascorbic Acid+Sodium Sulphate 6 healthy volunteers were given a 2 liter dose of each of A) Movicol, B) Movicol+ascorbic acid and C) Movicol+ascorbic acid+sodium sulphate and the volume of stools produced was measured. Movicol is a registered trademark of Norgine Limited and it is used in connection with a product of the formulation given in Table 2 below. The trial was carried out as a double blind cross-over study with 2 running periods for formulations A and B. Each volunteer was given formulation A and formulation B once each in a random order. The volunteers and the administering medical professional were blinded regarding which formulation was administered first. A third, open, study period was added for the investigation of formulation C. The composition of Movicol is shown in Table 2. The compositions of the three formulations are shown in Table 3.

TABLE 2

Composition per liter of Movicol

| Component | Quantity |
|---|---|
| Macrogol 3350 (PEG) | 105 g |
| Sodium bicarbonate | 1.428 g |
| Sodium chloride | 2.805 g |
| Potassium chloride | 0.373 g |
| Lime and lemon flavour* | 0.800 g |

*flavour SN292403 Lemon/Lime Nat. Trusil J2076 available from International Flavours and Fragrances (IFF)

TABLE 3

Compositions per liter of formulations A, B and C

| Compound | Form. A | Form. B | Form. C |
|---|---|---|---|
| Movicol | 1x | 1x | 1x |
| Saccharose (Vit. C placebo) | 10 g | 0 | 0 |
| Ascorbic acid | 0 | 10 g | 10 g |
| Sodium sulphate | 0 | 0 | 5.6 g |
| Osmolarity: mOsmol/kg | 200 | 228 | 346 |

The Osmolarity values given in Table 3 are calculated values based on the information of the composition of the formulation. Movicol has a calculated osmolarity of 171 mOsmol/kg. In the calculations, polyethylene glycol is assumed to have no ionic impurities and the pH is assumed to be such that ascorbic acid essentially completely associated.

Saccharose was included in Formulation A to minimise the taste differences between the formulations. Ascorbic acid has a flavour enhancing effect on bowel preparation formulations.

Each volunteer was given 2 liters of each formulation over two hours at a rate of 250 ml per 15 minutes. Stools were collected over eight hours following commencement of the treatment. The quantity of stools produced is shown in Table 4.

TABLE 4

Results of formulation comparison experiments

| Parameter | Form. A | Form. B | Form. C |
|---|---|---|---|
| Stool weight/g | 1465.2 ± 56.7 | 1862 ± 140.8 | 2735 ± 199 |
| Stool volume/l | 1.4 ± 0.0 | 1.8 ± 0.1 | 2.7 ± 0.2 |
| Weight of PEG in stools/g | 192.6 ± 16.6 | 197.0 ± 10.9 | 177.0 ± 6.8 |

TABLE 5

Statistical significance (p) of formulation comparison experiments

| Parameter | C vs A | C vs B | B vs A |
|---|---|---|---|
| Stool weight/g | <0.001 | 0.002 | 0.005 |
| Stool volume/l | <0.001 | 0.003 | <0.001 |
| Weight of PEG in stools/g | 0.63 | 0.45 | 0.92 |

As seen in Tables 4 and 5, addition of 10 g/l of ascorbic acid to a Movicol formulation leads to a statistically significant increase in stool weight and stool volume.

Furthermore, addition of 10 g/l of ascorbic acid and 5.6 g/l of sodium sulphate to a Movicol formulation leads to an even greater statistically significant increase in stool weight and volume. Preparation C caused almost double the stool weight and volume of preparation A to be excreted. Comparing the results for preparation B and preparation C, the stool weight and volume is increased by approximately 50% (statistical significance p=0.002 for stool weight, p=0.003 for stool volume).

The solutions containing ascorbic acid were reasonably well tolerated. Three volunteers experienced nausea whilst drinking preparation A (no ascorbic acid), whereas only two volunteers experienced nausea whilst drinking preparation B and only two volunteers experienced nausea whilst drinking preparation C. Solutions B and C were both considered to be more palatable than solution A. Solution C was, surprisingly, not considered to be less palatable than solution B. Furthermore, despite the fact that solution C was hypertonic, no adverse side effects were noted.

No other or serious adverse side effects were observed. A slight (not statistically significant) increase in blood potassium levels was recorded and a net increase in ascorbemia was observed in the volunteers after taking solutions including ascorbic acid.

In conclusion, addition of 10 g/l of ascorbic acid to a Movicol composition leads to a substantial and statistically significant increase in stool weight and stool volume. The weight and volume of stools is further dramatically increased in a statistically significant manner by the addition of 5.6 g/l sodium sulphate to the Movicol/ascorbic acid composition. The solution comprising Movicol, ascorbic acid and sodium sulphate was accordingly the most effective cleansing solution, and the improved effectiveness was surprisingly not accompanied by any adverse side effects or taste compromises.

Further trials in which the properties of compositions of the present invention are compared with compositions that are currently available also show that the compositions and methods of the present invention are ones with surprisingly superior properties.

Example 2

Comparison of Compositions of the Invention

A trial was carried out to investigate the effect on the efficacy of the cleansing solutions of the invention of altering, independently, the quantities of the PEG, sodium sulphate and ascorbic acid components. Six compositions were investigated. The formulations were made up as aqueous solutions comprising compositions, A to F. The amount of each component in compositions A to F per liter of formulation is shown in Table 6.

TABLE 6

Compositions A to F of the invention

| Comp. | PEG 3350 | Sodium Sulphate | Ascorbic Acid | Sodium Ascorbate | NaCl | KCl | Osmolarity mOsmol/kg |
|---|---|---|---|---|---|---|---|
| A | 100 | 7.5 | 0.0 | 0.0 | 2.691 | 1.058 | 308 |
| B | 100 | 7.5 | 5.0 | 0.0 | 2.691 | 1.058 | 337 |
| C | 100 | 7.5 | 5.0 | 5.0 | 2.691 | 1.058 | 379 |
| D | 100 | 7.5 | 10.0 | 0.0 | 2.691 | 1.058 | 365 |
| E | 100 | 5.0 | 5.0 | 5.0 | 2.691 | 0.819 | 329 |
| F | 125 | 7.5 | 5.0 | 5.0 | 3.217 | 1.155 | 416 |

NB All compositions were lemon flavoured. The lemon flavouring was Ungerer Lemon SDF obtained from RSSL Pharma.

Composition E (containing 100 g PEG, 5 g sodium sulphate, 5 g ascorbic acid, 5 g sodium ascorbate, electrolytes and flavour) was the reference composition for the study.

Volunteers were informed of the aims and procedures of the study and informed consent was obtained. A medical history was obtained from each volunteer and a physical examination was carried out. 30 Volunteers were recruited. Each volunteer was randomly assigned two different treatment compositions, so that, in total, each composition was tested 10 times. The testing of each composition took one day and the two tests for each volunteer were separated by a "washout" period of 7 to 15 days.

Urine samples were collected from each volunteer throughout the day before the clinical trial. The volunteers were instructed to fast overnight before the trial and, on the day of the trial, they arrived at the clinic at 8am. Each volunteer drank 2 liters of the allocated composition over a period of 2 hours (two 125 ml glasses approximately every 15 minutes). Stool volume and weight were assessed from the start of drinking and during the subsequent 8 hours. The volunteers were generally not allowed to eat during the test period but volunteers who complained of thirst and/or appeared dehydrated were allowed to drink water 4 hours after the beginning of the study.

Weight, blood pressure and pulse rate were measured before treatment and 8 hours after the start of the treatment, or as soon as necessary in the judgement of the investigator. A blood sample was taken 4 hours after the start of the treatment for analysis of serum electrolytes, urea, creatine, hematocrit and total protein. A second blood sample was frozen for later ascorbic acid evaluation. Urine was collected between the start of the treatment and the end of the test period. Electrolytes in urine were also assessed on a volume collected during the day of the trial. Another sample of urine was frozen for later ascorbic acid evaluation.

The volunteers gave an assessment of the taste of the preparation immediately after finishing drinking the total amount of the solution.

In case of drop-out, non-compliance, or a serious adverse event not related to the study, volunteers were replaced such that 30 useful sets of data were obtained. Similarly, any volunteers who needed any medication during the trial which might influence intestinal transit or interfere with the study medication were also replaced. In total 6 volunteers had to be replaced during the study.

Each volunteer was randomly given one of the 6 compositions for the first test and a different one of the 6 compositions for the second test. Each volunteer is thus its own control and the power of the study is increased. Each PEG composition had a similar visual appearance and after dissolution in water, the volume and aspect of the compositions were similar. The compositions had different tastes.

Most of the stools were delivered 4 hours after the start of the study.

Results of the Effectiveness of Compositions of the Invention

The volume and weights of stools collected during the study are shown in Table 7.

TABLE 7

| | Total stool volume and weight | | | | | |
|---|---|---|---|---|---|---|
| | A | B | C | D | E | F |
| Volume (l) | | | | | | |
| Mean | 1.926 | 2.249 | 2.613 | 2.510 | 2.195 | 2.555 |
| S.D. | 0.598 | 0.437 | 0.538 | 0.442 | 0.369 | 0.755 |
| Range | 0.65–2.62 | 1.58–2.84 | 1.80–3.40 | 1.44–3.08 | 1.49–2.60 | 1.17–3.50 |
| Weight (g) | | | | | | |
| Mean | 1992 | 2306 | 2684 | 2533 | 2283 | 2638 |
| S.D. | 625 | 437 | 567 | 442 | 381 | 745 |
| Range | 650–2744 | 1630–2920 | 1830–3557 | 1526–3150 | 1581–2765 | 1280–3513 |

The stools volume mean ranged between 1.9 and 2.6 liters.

As seen in Table 7 stool volume means for the six compositions range between 1.9 and 2.6 liters. Considering the mean values, compositions D, F and C resulted in a greater volume of stools than compositions B and E which in turn resulted in the greater volume of stools than composition A. The variability within each sample was greater than expected (average standard deviation 443 ml) and consequently a global comparison between the compositions was not statistically significant ($p<0.217$). Similar results were observed for stool weight ($p<0.318$). Four individual volunteers (one each in treatments A, B, C and F) did not adhere strictly to the protocol. In the case of composition B and composition F, a small amount of vomiting took place during the treatment intake for one of the subjects, and in the case of compositions A and C, a reduced quantity of composition solution was ingested (1000 cc and 1500 cc respectively) by one of the subjects. When the results were analysed excluding those treatments the statistical interpretation remained unchanged.

The time taken for the volunteers to ingest the treatment solutions was recorded and the results are shown in Table 8.

TABLE 8

| | Time for formulation intake | | | | | |
|---|---|---|---|---|---|---|
| Time (min) | A | B | C | D | E | F |
| Mean ± S.D. | 112.8 ± 7.5 | 115.7 ± 15.6 | 117.8 ± 16.7 | 116.7 ± 9.3 | 114.9–11.2 | 116.5 ± 13.3 |
| Range | 100–120 | 90–140 | 95–145 | 100–135 | 100–130 | 90–140 |

There was no correlation between formulation intake time and stools volume ($r=-0.125$ $p<0.340$).

Volunteers were asked to rate the taste of the solutions for salt, acid and sweetness on a scale of 0 to 3 in which 0=very pleasant, 1=not awkward, 2=tolerable and 3=intolerable. The results of the taste response are shown in Table 9.

TABLE 9

| | Taste scores | | | | | |
|---|---|---|---|---|---|---|
| | A | B | C | D | E | F |
| Salt | | | | | | |
| Mean ± S.D. | 2.6 ± 0.5 | 2.6 ± 0.5 | 2.4 ± 0.5 | 2.1 ± 0.6 | 2.1 ± 0.4 | 2.1 ± 0.4 |
| Range | 2–3 | 2–3 | 2–3 | 1–3 | 1–3 | 2–3 |
| Acid | | | | | | |
| Mean ± S.D. | 1.4 ± 0.7 | 2.0 ± 0.5 | 1.6 ± 0.5 | 1.9 ± 0.7 | 1.8 ± 0.4 | 1.8 ± 0.4 |
| Range | 0–2 | 1–3 | 1–2 | 1–3 | 1–2 | 1–2 |
| Syrupy | | | | | | |
| Mean ± S.D. | 2.1 ± 0.6 | 2.1 ± 0.4 | 2.1 ± 0.6 | 2.3 ± 0.7 | 2.1 ± 0 | 2.1 ± 0.6 |
| Range | 1–3 | 2–3 | 1–3 | 1–3 | 2–2 | 1–3 |

There was no significant difference between the solutions when assessed for saltiness (p<0.459) or sweetness (P<0.238). However, the assessment of acid taste of the different solutions was significantly different (p<0.039), composition A being the least acidic and composition B the most acidic. Composition A would be expected to be least acidic as it does not contain any ascorbic acid.

In terms of efficacy there were no global statistically significant differences between the compositions. This was mostly because of the large degree of variability. However, addition of 10 g ascorbic acid (ascorbic acid or mixture of ascorbic acids and sodium ascorbate) gave the best results. Treatments C and D were thus concluded to be the most effective solutions.

Clinical Laboratory Evaluation

The stools were analysed for ion contents. The results for composition D are shown in Table 10.

TABLE 10

Stool ionogram results for composition D

|  | Ionogram (mmol/liter) | Ionogram (mmol) |
|---|---|---|
| $Na^+$ | | |
| N | 10 | 10 |
| Mean ± S.D. | 109.6 | 276.6 ± 59.4 |
| Range | 97–122 | 148.3–375.8 |
| $K^+$ | | |
| N | 10 | 10 |
| Mean ± S.D. | 14.9 ± 4.7 | 36.8 ± 12.2 |
| Range | 8–25 | 24.6–64.3 |
| $Cl^-$ | | |
| N | 10 | 10 |
| Mean ± S.D. | 26.8 ± 6.8 | 68.2 ± 25.8 |
| Range | 19–42 | 36.0–129.4 |

There were no statistically significant differences between the ionograms of the six different treatments.

The hematocrit % was measured before and after treatment and the results for composition D are shown in Table 11.

TABLE 11

% Hematocrit before and after treatment for composition D

|  | % Hematocrit |
|---|---|
| Before | |
| N | 10 |
| Mean ± S.D. | 42.1 ± 4.4 |
| Range | 31.7–46.0 |
| After | |
| N | 8 |
| Mean ± S.D. | 43.3 ± 5.6 |
| Range | 29.8–48.3 |
| Difference | |
| N | 9 |
| Mean ± S.D. | 1.47 ± 0.52 |

Multiple comparisons between % hematocrit for the different compositions revealed no statistically significant differences. Similar results were obtained for compositions A, B, C, E and F.

Sodium, potassium, chloride and bicarbonate concentrations in the blood were measured before and after ingestion of the compositions. The results are shown in Tables 12, 13, 14 and 15.

TABLE 12

Change in blood sodium concentration (mmol/l)

|  | A | B | C | D | E | F |
|---|---|---|---|---|---|---|
| Before | | | | | | |
| N | 10 | 10 | 9 | 10 | 9 | 10 |
| Mean ± S.D. | 141.0 ± 1.4 | 140.4 ± 1.2 | 140.8 ± 1.6 | 141.7 ± 2.0 | 140.7 ± 2.4 | 140.9 ± 2.5 |
| Range | 139–143 | 139–142 | 139–143 | 139–145 | 137–144 | 137–145 |
| After | | | | | | |
| N | 10 | 10 | 10 | 10 | 10 | 10 |
| Mean ± S.D. | 143.5 ± 2.3 | 142.5 ± 2.5 | 143.8 ± 1.2 | 143.6 ± 2.3 | 143.7 ± 2.1 | 145.4 ± 2.2 |
| Range | 139–148 | 137–146 | 142–146 | 140–146 | 140–147 | 141–148 |
| Difference | | | | | | |
| N | 10 | 10 | 9 | 10 | 9 | 10 |
| Mean ± S.D. | 2.5 ± 0.79 | 2.1 ± 0.89 | 3.22 ± 0.66 | 1.9 ± 0.59 | 2.86 ± 1.09 | 4.5 ± 0.78 |

As seen in Table 12 a borderline significant difference was observed between compositions B and C (p=0.053). A statistically significant difference was seen between compositions B and F (p=0.016) and between compositions E and F (p=0.039). Composition F caused the largest increase in blood sodium levels.

TABLE 13

Change in blood potassium concentration (mmol/l)

|  | A | B | C | D | E | F |
|---|---|---|---|---|---|---|
| Before |  |  |  |  |  |  |
| N | 10 | 10 | 9 | 10 | 9 | 10 |
| Mean ± S.D. | 4.1 ± 0.4 | 4.0 ± 0.2 | 4.0 ± 0.2 | 4.0 ± 0.3 | 4.1 ± 0.2 | 3.9 ± 0.2 |
| Range | 3.5–4.5 | 3.7–4.3 | 3.7–4.5 | 3.4–4.5 | 3.7–4.4 | 3.5–4.2 |
| After |  |  |  |  |  |  |
| N | 10 | 10 | 10 | 10 | 10 | 10 |
| Mean ± S.D. | 4.1 ± 0.4 | 4.4 ± 0.3 | 4.5 ± 0.3 | 4.6 ± 0.2 | 4.2 ± 0.4 | 4.3 ± 0.3 |
| Range | 3.3–4.6 | 4.0–4.9 | 4.0–5.0 | 4.2–4.9 | 3.5–5.0 | 3.9–4.8 |
| Difference |  |  |  |  |  |  |
| N | 10 | 10 | 9 | 10 | 9 | 10 |
| Mean ± S.D. | 0.08 ± 0.09 | 0.41 ± 0.11 | 0.51 ± 0.10 | 0.61 ± 0.13 | 0.19 ± 0.14 | 0.43 ± 0.07 |

Multiple comparisons showed no significant difference between the compositions.

TABLE 14

Change in blood chloride concentration (mmol/l)

|  | A | B | C | D | E | F |
|---|---|---|---|---|---|---|
| Before |  |  |  |  |  |  |
| N | 10 | 10 | 9 | 10 | 9 | 10 |
| Mean ± S.D. | 102.3 ± 1.6 | 101.4 ± 2.5 | 102.1 ± 1.4 | 102.5 ± 2.3 | 102.3 ± 1.7 | 103.3 ± 2.6 |
| Range | 100–105 | 98–105 | 100–104 | 100–107 | 100–105 | 100–107 |
| After |  |  |  |  |  |  |
| N | 10 | 10 | 10 | 10 | 10 | 10 |
| Mean ± S.D. | 105.6 ± 1.8 | 106.2 ± 3.2 | 106.4 ± 2.4 | 107.4 ± 2.4 | 105.7 ± 1.5 | 108.9 ± 3.3 |
| Range | 103–108 | 102–112 | 104–112 | 104–111 | 104–108 | 105–114 |
| Difference |  |  |  |  |  |  |
| N | 10 | 10 | 9 | 10 | 9 | 10 |
| Mean ± S.D. | 3.3 ± 0.80 | 4.8 ± 0.87 | 4.44 ± 0.80 | 4.9 ± 0.41 | 3.22 ± 0.62 | 5.6 ± 0.69 |

As seen in Table 14 a difference of border line statistical significance was observed between compositions A and D (p=0.056). A significant difference was observed between compositions A and F (p=0.010), compositions B and F (p=1.036), compositions D and E (p=0.031) and compositions E and F (p=0.005). Composition F caused the largest increase in blood chloride concentration.

TABLE 15

Change in blood bicarbonate concentration (mmol/l)

|  | A | B | C | D | E | F |
|---|---|---|---|---|---|---|
| Before |  |  |  |  |  |  |
| N | 10 | 10 | 9 | 10 | 9 | 10 |
| Mean ± S.D. | 26.9 ± 3.3 | 28.2 ± 2.0 | 28.6 ± 2.1 | 28.9 ± 2.0 | 28.4 ± 2.1 | 26.3 ± 3.2 |
| Range | 19–30 | 25–31 | 26–32 | 26–32 | 25–32 | 20–31 |
| After |  |  |  |  |  |  |
| N | 10 | 10 | 10 | 10 | 10 | 10 |
| Mean ± S.D. | 26.7 ± 3.3 | 26.1 ± 2.1 | 26.6 ± 1.9 | 25.5 ± 1.8 | 26.1 ± 2.2 | 25.6 ± 2.5 |
| Range | 25–29 | 24–31 | 24–30 | 22–27 | 22–30 | 23–31 |

TABLE 15-continued

| Change in blood bicarbonate concentration (mmol/l) | | | | | |
|---|---|---|---|---|---|
| A | B | C | D | E | F |

Difference

| | | | | | |
|---|---|---|---|---|---|
| N | 10 | 10 | 9 | 10 | 9 | 10 |
| Mean ± S.D. | −0.2 ± 0.80 | −2.1 ± 0.82 | −1.78 ± 0.60 | −3.4 ± 0.60 | −1.89 ± 0.72 | −0.7 ± 0.75 |

Multiple comparisons showed a significant difference between compositions A and D (p=0.010) and between compositions E and F (p=0.035)

Blood urea, creatinemia and protidemia were measured. The results for composition D are shown in Table 16.

TABLE 16

Change in Blood urea, creatinemia and protidemia for composition D

| | Urea (mmol/l) | Creatinemia (mmol/liter) | Protidemia (g/l) |
|---|---|---|---|
| Before | | | |
| N | 10 | 10 | 10 |
| Mean ± S.D. | 4.9 ± 0.9 | 81.4 ± 11.9 | 75.3 ± 4.8 |
| Range | 3.6–6.3 | 64–98 | 69–83 |
| After | | | |
| N | 10 | 10 | 10 |
| Mean ± S.D. | 4.5 ± 1.0 | 80.9 ± 13.6 | 78.9 ± 5.8 |
| Range | 2.6–5.8 | 59–98 | 70–87 |
| Difference | | | |
| N | 10 | 10 | 10 |
| Mean ± S.D. | −0.39 ± 0.21 | −0.50 ± 1.66 | 3.60 ± 1.77 |

Multiple comparisons between the compositions showed no significant differences. Similar results were obtained for compositions A, B, C, E and F.

Multivariate analysis of differences for all biological parameters showed no significant results.

Urine was also analysed for sodium, potassium and chloride content. The results for the group of volunteers given composition D are shown in Table 17.

TABLE 17

Change in urine sodium, potassium and chloride content for composition D

| | Sodium Content (mmol) | Potassium content (mmol) | Chloride content (mmol) |
|---|---|---|---|
| Before | | | |
| N | 10 | 10 | 9 |
| Mean ± S.D. | 63.6 ± 33.8 | 38.9 ± 21.3 | 69.8 ± 34.6 |
| Range | 23.5–105.0 | 7.8–69.0 | 19.7–112.0 |
| After | | | |
| N | 10 | 10 | 10 |
| Mean ± S.D. | 46.6 ± 47.1 | 24.8 ± 20.8 | 53.7 ± 48.4 |
| Range | 3.1–161.6 | 4.9–64.8 | 6.8–164.8 |

A slight, not statistically significant, decrease in the level of urine sodium, potassium and chloride was observed.

There was no statistically significant difference between the composition treatment groups. Similar results were obtained for compositions A, B, C, E and F.

Ascorburia was also measured and the results are shown in Tables 18 and 19.

TABLE 18

| Ascorburia (μmol/liter) | | | | | |
|---|---|---|---|---|---|
| | A | B | C | D | E | F |
| N | 8 | 8 | 7 | 7 | 4 | 4 |
| Mean | 445.3 | 5266.9 | 7292.1 | 8408.6 | 8046.3 | 2556.5 |
| S.D. | 668.3 | 4402.9 | 1781.4 | 9641.3 | 2437.7 | 3690.4 |
| Range | 17–1756 | 158–15141 | 4913–9463 | 129–28390 | 4482–9835 | 338–8043 |

TABLE 19

| Ascorburia (μmol) | | | | | |
|---|---|---|---|---|---|
| | A | B | C | D | E | F |
| N | 8 | 8 | 7 | 7 | 4 | 4 |
| Mean | 154.3 | 1690.1 | 2631.3 | 2152.1 | 2423.6 | 1141.2 |
| S.D. | 223.0 | 1473.1 | 1134.9 | 1856.4 | 1406.1 | 1818.1 |
| Range | 2.5–527 | 47–4845 | 1103–4216 | 77–5678 | 448–3740 | 108–3861 |

There was no significant differences between compositions in terms of μmol/lire or μmol ascorburia (pc 0.303 and pc 0.641 respectively). As expected, composition A showed the lowest level of ascorburia because the solution did not contain any ascorbic acid or sodium salts.

In conclusion, all biochemical alterations were without clinical significance and all compositions were clinically and biologically well tolerated.

Conclusions of Experiments Directed to Compositions of the Invention:

TABLE 20

Summary of results for compositions A to F

| Comp | PEG 3350 | Ingredient (g) Sodium Sulphate | Ascorbic Acid | Sodium Ascorbate | Osmol. mOsmol/ kg | Mean Stool Volume l | Mean Decrease in $HCO_3^-$ mmol/l |
|---|---|---|---|---|---|---|---|
| A | 100 | 7.5 | 0.0 | 0.0 | 308 | 1.9 | 0.2 |
| B | 100 | 7.5 | 5.0 | 0.0 | 337 | 2.2 | 2.1 |
| C | 100 | 7.5 | 5.0 | 5.0 | 379 | 2.6 | 1.8 |
| D | 100 | 7.5 | 10.0 | 0.0 | 365 | 2.5 | 3.4 |
| E | 100 | 5.0 | 5.0 | 5.0 | 329 | 2.2 | 1.9 |
| F | 125 | 7.5 | 5.0 | 5.0 | 416 | 2.6 | 0.7 |

As is seen from the data in Table 20, compositions comprising 7.5 g sodium sulphate (A, B, C, D and F) gave rise to larger volume of stools than the composition comprising only 5 g sodium sulphate (E). No significant difference was observed between equivalent solutions containing 100 g polyethylene glycol (C) and 125 g polyethylene glycol (F). Compositions containing ascorbic acid and/or sodium ascorbate (B, C, D, E and F) gave rise to larger volumes of stools than the composition without ascorbic acid or sodium ascorbate (A). Compositions containing 10 g ascorbic acid (D) or 5 g ascorbic acid plus 5 g sodium ascorbate (C, E and F) gave rise to a larger volume of stools than compositions containing 5 g ascorbic acid alone (B). The preparation containing 100 g polyethylene glycol, 7.5 g sodium sulphate and 10 g ascorbic acid induced a clinically significant fall in plasma bicarbonate levels (D). That fall was not observed in the case of the composition containing 100 g polyethylene glycol, 7.5 g sodium sulphate, 5 g ascorbic acid and 5 g sodium ascorbate (C).

Weight loss was around 1 kg for all volunteers despite a decrease in urinary volume (200–300 ml over 8 hours). Protidemia and haematocrit were increased explaining a slight dehydration. Natremia and kaliemia were also slightly increased. Polyethylene glycol concentration in stools was assessed in treatment groups D and F only. Stool volumes correlated roughly to the amount of PEG measured in the collected stools.

Example 3

Study of Ingestion of Colon Cleansing Composition Interspersed with Water Ingestion Ten subjects were enrolled for the study and written informed consent was given before its commencement. Each volunteer was given 2 liters of composition D as defined in Example 2. The composition was administered according to two different modes of administration on two different occasions separated by a wash-out period. In administration mode 1, the volunteer drank 2 liters of composition D within 2 hours as in the case of Example 2. According to administration mode 2 the volunteer drank 1 liter of composition over 1 hour, followed by 500 ml water over the next hour, followed by a second liter of composition over the following hour, followed by 1000 ml water over the following 2 hours.

Stools were collected over the 8 hours following commencement of the administration. A comparison of stool weights obtained by the two modes of administration is shown in Table 21.

TABLE 21

Comparison of stool weight according to mode of administration

| Weight (g) | Mode 1 | Mode 2 |
|---|---|---|
| N* | 9 | 9 |
| Mean | 2464 | 2726 |
| S.D. | 409 | 198 |
| Range | 1526–2865 | 2350–2920 |

*Number of subjects

The volume of stools generated following administration of composition D is increased by around 300 ml using mode 2 as compared with mode 1. When asked to rate their impression of the tolerability of the treatment on a visual analogue scale (VAS) on which 0 mm=excellent appreciation and 100 mm=very bad appreciation the tolerability was ranked as shown in Table 22.

TABLE 22

Comparison of tolerability VAS according to mode of administration

| VAS (mm) | Mode 1 | Mode 2 |
|---|---|---|
| N | 9 | 9 |
| Mean ± S.D. | 68.4 ± 20.0 | 59.4 ± 21.0 |
| Range | 35–98 | 17–85 |

A statistically significant decrease (p<0.0276) of 10 mm on the VAS scale in favour of better tolerability for mode 2 of administration was observed. Among nine subjects, eight preferred the second mode of administration.

Example 4

Assessment of Efficacy and Safety of Colon Cleansing Solution in Patients Undergoing Endoscopy 30 patients (12 male, 18 female, mean age 51+/−11) were given 2 liters of a colon cleansing composition comprising for one liter of solution the materials as shown in Table 23

TABLE 23

Endoscopy experiment colon cleansing solution

| Material | Weight (g) per 1 preparation |
|---|---|
| PEG 3350 | 100.0 |
| Sodium Sulphate | 7.5 |
| Ascorbic Acid | 4.7 |
| Sodium Ascorbate | 5.9 |
| Sodium Chloride | 2.69 |
| Potassium Chloride | 0.93 |
| Lemon Flavour | 2.015 |
| Citric Acid Anhydrous | 1.565 |
| Acesulfame K | 0.35 |
| Calculated osmolarity | 392 mOsmol/kg |

The colon cleansing solution was given in a regime as follows:

First hour: 1 liter of solution ingested orally
Second hour: 0.5 liter water ingested orally
Third hour: 1 liter of solution ingested orally
Fourth hour: at least 0.5 liter water ingested orally within 1.5 hours The cleanliness of the colon was assessed by the colonoscopist on a 4 point scale (very good for all colon segments=grade 4, good for all colon segments=grade 3, at least one colon segment with totally or partially removable residual faeces=grade 2 or 1, at least one colon segment with heavy hard stools=grade 0). The scores were then ranked as A for grade 3 or 4, B for grade 1 or 2 and C for grade 0. The investigator judged the quality of colon preparation as very good or good in 20 patients, in at least one section moderate in 6, bad in 3 and very bad in 1, leading to a final scoring of 20A, 9B and 1C.

The mean weight of stools was 2866+/−667 g and the mean volume of fluid removed from the colon during colonoscopy was 130+/−124 ml. The digestive tolerance of the preparation was good in 26 patients, moderate in 2 and poor in 2. Only one patient experienced profuse vomiting. No statistically significant changes in blood chloride or bicarbonate ion concentrations were observed over the period of the treatment.

Example 5

Formulation Examples

Flavoured Product Formulation 1

TABLE 23

UNGERER LEMON Composition

| Material | % w/w | Weight (g) per 125 ml preparation |
|---|---|---|
| Movicol Base | 96.275 | 13.7008 |
| Acesulfame K | 0.321 | 0.0455 |
| Talin | 0.058 | 0.0082 |
| NHDC | 0.058 | 0.0082 |
| Citric Acid | 0.078 | 0.0110 |
| Natrosol 250 M | 1.840 | 0.2606 |
| Lemon | 0.920 | 0.1303 |

Talin is a taste enhancer comprising Thaumatin (available from The Talin Food Company, Merseyide, England). NHDC (neohesperidine dihydrochloride) is a sweetener, (available from Evesa, P.O. Box 103, 11300 La Linea de la concepcion, Cádiz, Spain). Natrosol 250M is a hydroxyethylcellulose available from Hercules Incorporated via Aqualon.

Flavoured Product Formulation 2

TABLE 24

UNGERER STRAWBERRY Composition Product

| Material | % w/w | Weight (g) per 125 ml preparation |
|---|---|---|
| Movicol Base | 97.603 | 13.7008 |
| Acesulfame K | 0.325 | 0.0456 |
| NHDC | 0.014 | 0.0020 |
| Natrosol 250 M | 1.858 | 0.2608 |
| Strawberry | 1.800 | 0.2527 |

Flavoured Product Formulation 3

TABLE 25

IFF Grapefruit flavouring Composition

| Material | % w/w | Weight (g) per 21 preparation |
|---|---|---|
| PEG 3350 | 79.24 | 200.0 |
| Sodium Sulphate | 5.94 | 15.0 |
| Ascorbic Acid | 3.96 | 10.0 |
| Sodium Ascorbate | 3.96 | 10.0 |
| Sodium Chloride | 2.13 | 5.38 |
| Potassium Chloride | 0.84 | 2.12 |
| IFF Grapefruit Flavouring Powder | 2.41 | 6.08 |
| Citric Acid Anhydrous | 1.23 | 3.10 |
| Acesulfame K | 0.28 | 0.70 |
| Calculated osmolarity | 392 mOsmol/kg | 392 mOsmol/kg |

Flavoured Product Formulation 4

TABLE 26

UNGERER BLACKCURRANT Composition

| Material | % w/w | Weight (g) per 21 preparation |
|---|---|---|
| PEG 3350 | 79.81 | 200.0 |
| Sodium Sulphate | 5.99 | 15.0 |
| Ascorbic Acid | 3.99 | 10.0 |
| Sodium Ascorbate | 3.99 | 10.0 |
| Sodium Chloride | 2.15 | 5.38 |
| Potassium Chloride | 0.85 | 2.12 |
| Ungerer Blackcurrant | 1.62 | 4.06 |
| Citric Acid Anhydrous | 1.24 | 3.10 |
| Acesulfame K | 0.28 | 0.70 |
| Talin | 0.08 | 0.20 |
| Calculated osmolarity | 392 mOsmol/kg | 392 mOsmol/kg |

Flavoured Product Formulation 5

TABLE 27

IFF Pineapple flavouring

| Material | % w/w | Weight (g) per 21 preparation |
|---|---|---|
| PEG 3350 | 79.81 | 200.0 |
| Sodium Sulphate | 5.99 | 15.0 |
| Ascorbic Acid | 3.99 | 10.0 |
| Sodium Ascorbate | 3.99 | 10.0 |
| Sodium Chloride | 2.15 | 5.38 |
| Potassium Chloride | 0.85 | 2.12 |
| IFF Pineapple Flavouring Powder | 1.70 | 4.06 |
| Citric Acid Anhydrous | 1.26 | 3.10 |
| Acesulfame K | 0.29 | 0.70 |
| Calculated osmolarity | 392 mOsmol/kg | 392 mOsmol/kg |

Flavoured Product Formulation 6

TABLE 28

IFF Vanilla + Givaudan-Roure Lemon and Lime Flav-o-lok Composition

| Material | % w/w | Weight (g) per 21 preparation |
|---|---|---|
| PEG 3350 | 78.95 | 200.0 |
| Sodium Sulphate | 5.92 | 15.0 |
| Ascorbic Acid | 3.95 | 10.0 |
| Sodium Ascorbate | 3.95 | 10.0 |
| Sodium Chloride | 2.12 | 5.38 |
| Potassium Chloride | 0.84 | 2.12 |
| IFF Vanilla Flavouring Powder | 1.61 | 4.07 |
| Givaudan-Roure Lemon and Lime Flav-o-lock | 1.15 | 2.91 |
| Citric Acid Anhydrous | 1.22 | 3.09 |
| Acesulfame K | 0.29 | 0.70 |
| Calculated osmolarity | 392 mOsmol/kg | 392 mOsmol/kg |

In the following examples, the ascorbic acid and sodium ascorbate components are packaged separately from the other components to improve their stability.

a) Citric Acid-Containing Composition

The composition is provided in two sachets. The contents of the two sachets together are for making up to one liter of colon cleansing solution by addition of water.

| SACHET 1 | |
|---|---|
| PEG 3350: | 100.000 g |
| Sodium Sulphate: | 7.500 g |
| Sodium Chloride: | 2.691 g |
| Potassium Chloride: | 0.930 g |
| Anhydrous Citric Acid: | 1.565 g |
| Acesulfame K: | 0.350 g |
| Lemon Flavour: | 2.015 g |
| TOTAL WEIGHT OF SACHET 1 INGREDIENTS | 115.051 g |

| SACHET 2 | |
|---|---|
| Ascorbic Acid: | 4.700 g |
| Sodium Ascorbate: | 5.900 g |
| TOTAL WEIGHT OF SACHET 2 INGREDIENTS | 10.600 g | b) Aspartame-Containing Composition

The composition is provided in two sachets. The contents of the two sachets together are for making up to one liter of colon cleansing solution by addition of water.

| SACHET 1 (in grams per liter) | |
|---|---|
| PEG 3350: | 100.000 g |
| Sodium Sulphate: | 7.500 g |
| Sodium Chloride: | 2.691 g |
| Potassium Chloride: | 1.015 g |
| Aspartame: | 0.233 g |
| Acesulfame K: | 0.117 g |
| Lemon Flavour (Ungerer V3938-1N1) | 0.340 g |
| TOTAL WEIGHT OF SACHET 1 INGREDIENTS | 111.896 g |

| SACHET 2 (in grams per liter) | |
|---|---|
| Ascorbic Acid: | 4.700 g |
| Sodium Ascorbate: | 5.900 g |
| TOTAL WEIGHT OF SACHET 2 INGREDIENTS | 10.600 g |

COMPARATIVE EXAMPLES

Various investigations were made into the reduction of the volume of solutions of the prior art required to achieve satisfactory colon clearance. Stimulant laxatives, for example bisacodyl, picosulphate or senna, were added to a GoLYTELY solution. They were effective in achieving clearance of the bowel, but the risk of plasma electrolyte disturbances was increased. In a further experiment, a hyperconcentrated GoLYTELY solution (powder for two one-liter doses made up to only one liter) was found to be effective in the clearance of the bowel, but the solution was unpalatable, that is to say, participants in the trial found the taste of the solution so unpleasant that ingestion of the solution was very difficult. In the absence of direct supervision by a medical professional, that degree of unpalatablity is likely to lead to patient non-compliance.

Example 6

Clinical Trials

Two phase III clinical trials were performed with the aim of demonstrating safety equal to that of a polyethylene glycol+electrolytes composition (PEG+E) and patient acceptance equal to that of sodium phosphate solutions, both of which are preparations in current use for gut cleansing prior to colonoscopy.

Clinical Trial 1

Study Centre(s):

Multi-centre clinical trial involving a total of 12 specialised gastroenterology units in Germany.

Objectives:

To demonstrate that the oral gut cleansing solution NRL994 (see below) is not less effective than the current standard treatment (PEG+E, Klean-Prep®, see below) with regard to the overall quality of bowel preparation in patients scheduled to receive colonoscopy.

Methodology:

The study was carried out as a randomised, single-blind, active-controlled, multi-centric, non-inferiority phase III study with two parallel treatment groups. Patients were hospital in-patients and enrolled one or two days prior to the elective endoscopic procedure. Both investigational products were taken in two equal split doses; gut cleaning started in the evening prior to the intervention when the first half of the cleansing solution was to be taken; bowel preparation was continued in the morning of colonoscopy with the second half of the dose. A patient's participation in the study ended after completion of the endoscopic procedure.

Number of subjects:

362 hospital inpatients scheduled to undergo complete colonoscopy were enrolled.

Diagnosis and criteria for inclusion:

Male or female in-patients, having given their written informed consent, 18 to 85 years old, scheduled for colonoscopy, with no history of colonic surgery, without contraindications for colonoscopy or the treatment with NRL994.

Test product NRL 994, dose, mode of administration

Test product: One dose of NRL994 consists of 100 g PEG 3350, 7.5 g sodium sulphate, 4.7 g ascorbic acid, 5.9 g sodium ascorbate, 46 mmol sodium chloride, and 12.46 mmol potassium chloride. The product is flavoured with lemon flavour (2.015 g), anhydrous citric acid (1.565 g), and potassium acesulfame (0.35 g). (The product is the same as that used in Example 4, see Table 23.) The powder of one dose is to be diluted in 1,000 ml of water.

Total dose: Two doses each of 1 liter (total 2 liters).

Methodology: Each dose of one liter of NRL994 to be swallowed within one hour, followed by 500 ml of additional clear fluid.

Duration of Treatment:

Intake of NRL994 was in two split doses of one liter each, separated by a nocturnal pause: the first dose had to be taken in the afternoon or evening before the intervention (until 22:00) and the second dose in the morning of colonoscopy (from 06:00 onwards). A time interval of at least one hour was required between the end of intake and the start of colonoscopy.

Reference Therapy, Dose, Mode of Administration:

Reference product: PEG+E (Klean-Prep®) consisted of 59 g PEG 3350, 5.7 g sodium sulphate, 1.5 g sodium chloride, 0.7 g potassium chloride, and 1.7 g sodium bicarbonate. The product was flavoured with vanilla flavour and sweetener. The powder of one dose was to be diluted in 1,000 mL of water.

Total dose: Four doses each of 1 liter (total 4 liters)

Methodology: One liter had to be swallowed within one hour (250 ml per 15 min).

Duration of Treatment:

Intake of the four doses of PEG+E (Klean-Prep®) was also in split amounts, separated by a nocturnal pause: two doses (2 liters) had to be taken in the afternoon or evening before the intervention (until 22:00) and further two doses (2 liters) in the morning of colonoscopy from 05:00 onwards. A time interval of at least one hour was required between the end of intake and the start of colonoscopy.

Concomitant Medication:

Concomitant administration of other products known to have a gut-cleansing action (gut lavage solutions, potent laxatives, enemas) was not allowed.

Assessment of Compliance:

Patients were provided with detailed instructions on how to prepare and use NRL994 or PEG+E (Klean-Prep®) solution; in most cases the medication was taken under nurse supervision. Additionally, patient compliance was assessed by comparing the number of sachets dispensed with that of sachets used. The actual volumes of NRL994 or PEG+E (Klean-Prep®) solution ingested and any remaining amounts were to be recorded by each patient.

| Criteria for evaluation: | |
|---|---|
| Schedule: | |
| Day −2 or Day −1: | assessment of eligibility, basis medical and laboratory examination; |
| Day −1: | in the evening start of bowel preparation (first dose of NRL994 or first two doses of PEG+E [Klean-Prep ®]; |
| Day 0: | in the morning completion of bowel preparation (second dose of NRL994 or last two doses of PEG+E [Klean-Prep ®], followed by colonoscopy at least one hour after having completed intake of the last dose. |

Criteria for evaluating efficacy:

The primary efficacy criterion was the overall quality of gut cleansing as judged by a blinded and independent gastroenterology expert panel on the basis of the videotapes recorded during the colonoscopy procedure. Other end points were the degree of gut cleansing per defined gut segment, overall quality of gut cleansing by the local endoscopist, overall use of the gut lavage solution and the overall easiness to perform the colonoscopy. Patient acceptance was documented via a diary card for the following parameters: evaluation of taste, global evaluation of taste, degree of patient's satisfaction, overall patient's acceptability and patient's compliance with the volume intake and diet restrictions. In addition, the safety and tolerability was evaluated.

Statistical methods:

The primary objective of the study was to demonstrate that the gut cleansing effect of a low-volume NRL994 is not worse than that of a high-volume standard gut cleansing regimen (PEG+E). Non-inferiority of NRL994 was to be concluded if the lower limit of the one-sided 97.5% confidence interval of the difference in success rates between the two treatment groups did not exceed −15%.

A per-protocol analysis (PPA) and an intention-to-treat analysis (ITT) were carried out. While the first was exclusively based on the ratings of the independent expert panel, in the latter missing results of the expert panel were replaced by the ratings of the colonoscopist; patients in whom neither rating was available were handled as treatment failures. In addition, modified intention-to-treat analyses (mITT) were performed using a different definition of treatment compliance for patients assigned to this dataset.

The primary efficacy analysis was performed on the basis of the per-protocol population and using the success rates calculated from the ratings by the independent expert panel.

Parametric data were analysed by means of usual standard summary statistics (mean, SD, median, min., max.); for categorical data frequency tables were calculated.

Summary of Results:

This study was a non-inferiority study for an efficacy parameter (gut cleansing). A total of 362 patients were enrolled. Two patients discontinued the study before randomisation and intake of the study medication. One additional patient was withdrawn after randomisation because of allergy to the vanilla flavour in PEG+E. A total of 359 patients (NRL994: n=180 and PEG+E: n=179) received at least some amounts of the study medication (ITT population). The average age of the included patients was about 60 years (NRL994: 58,0±16,0 years). The ITT and PP analysis showed for colon cleansing a non-inferiority of NRL994 versus PEG+E with a successful rate of colon cleansing of 88.9% for NRL994 versus 94.8% for PEG+E. Overall, the efficacy results show that the low volume (2 liters) intake of NRL994 is clinically non-inferior (±15%) to the bowel preparation using a standard large volume (4 liter) PEG+E preparation, which is regarded as gold standard. Patients consistently and statistical significantly preferred NRL994 over PEG+E on the basis of several parameters assessing patients acceptance, including taste and volume intake. NRL994 was as PEG+E safe and generally well tolerated. No serious adverse events were observed. The most frequently observed adverse events were treatment-related malaise, nausea, abdominal pain and vomiting. No difference was seen between NRL994 and PEG+E.

In summary, NRL994 is as effective and safe as PEG+E and, importantly, provides an improved patient acceptance related to the lower volume intake.

Clinical trial 2:

Investigators:

17 specialised hospital endoscopist physicians; 4 expert reviewers selected among the 17 investigators.

Study Centre(s):

17 specialised hospital endoscopic centres located in France.

Objectives:

To assess the equivalence of efficacy and to compare the safety of NRL994 versus an NaP solution for gut cleansing prior to coloscopy.

Methodology:

Randomised, single-blind (investigator), multicentre, active-controlled study in two parallel groups and evaluator-blinded for the primary variable of efficacy.

Number of Patients:

Male 181, Female 171, total 352.

Diagnosis and Inclusion Criteria:

Male or female having given their written informed consent, out and inpatients 18 to 75 years old, sent to the endoscoptic warm for diagnostic or therapeutic coloscopy.

Exclusion Criteria:

Age <18 or >75 years old,

Illeus,

Suspected intestinal occlusion or performation,

Toxic or congenical megacolon,

History of colonic resection,

Patients with Crohn's Disease or Ulcerative Colitis,

Congestive heart failure NYHA III or IV,

Documented renal insufficiency history with creatinine >170 microM/L,

Known hypersensitivity to polyethylene glycols or Na phosphate and/or Vitamin C, Known deficiency in G6PD, phenylketonuria, Concurrent participation in an investigational drug study or participation within 90 days of study entry, Females who are pregnant, or planning a pregnancy, females of child bearing potential not using reliable methods of contraception, Subject has a condition or is in a situation which in the investigators opinion may put the subject at significant risk, may confound the study results, or may interfere significantly.

Test Product, Dose, Mode of Administration:

Test product: NRL994 (see above).

Total dose: Two doses of NRL994, each of 1 liter (total 2 liters).

Methodology: Each liter to be drunk within 1 hour. Furthermore, at least 1000 ml (or more) of any additional clear fluid except milk to be taken after the 2 liters of NRL994.

Reference Therapy, Dose, Mode of Administration:

Reference product: NaP solution (Fleet Phospho Soda®)

Dose & methodology: The treatment (1 pack) consists of 2 flasks each of 45 ml. Each flask contains 21.6 g monobasic sodium phosphate monohydrate with 8.1 g dibasic sodium phosphate heptahydrate in a buffered aqueous solution. Each flask to be dissolved in 125 ml of water. Each intake of NaP solution to be preceded and followed by 250 ml (or more if necessary) of clear drinks (not milk). There must be delay of at least 12 hours between the intake of the two doses of 45 ml of NaP solution. In addition, 750 ml more of clear liquids (not milk) or more if needed must be drunk between the two intakes.

Duration of Treatment:

Both treatments to be taken the day before the coloscopy procedure.

Criteria for Evaluation:

The primary endpoint was the overall quality of gut cleansing as judged by an endoscopist coming from a panel of endoscopist reviewers, blinded from the preparation allocated, on the basis of the videotapes recorded during the colonscopy procedure. Other efficacy endpoints were the overall quality of gut cleansing and global evaluation by the local endoscopist. Patient acceptance was documented via a diary card for following parameters: global patient's satisfaction with the bowel preparation, volume drunk, easiness to drink the gut lavage solution, comply with the diet restrictions, willingness to drink again the same bowel preparation and the taste. In addition, the safety and tolerability was evaluated.

Statistics:

As clinical trial 1.

Summary of Results:

This study is an equivalence study for an efficacy parameter (gut cleansing). A total of 352 patients were enrolled. Six patients from each group were excluded from all analysis. A total of 340 patients (NRL994: n=169 and NaP: n=171) received at least some amounts of the study medication (ITT population for safety). Average age of the included patients was about 53 years for both groups. The ITT and PP analysis showed for colon cleansing an equivalence of NRL994 to NaP with a successful rate of colon cleansing of 72.5% for NRL994 versus 63.9% for NaP (observed advantage for NRL994 over NaP was +8.6%, n.s.). Overall, the efficacy results show that the 2 liters intake of NRL994 is clinically equivalent to the bowel preparation using a NaP solution.

The acceptability parameters for the NRL994 bowel preparation demonstrated significant advantages compared to NaP with improved taste, effect on personal activities, diet recommendation and willingness to take the same bowel preparation again. NaP was preferred for compliance and easiness to drink the bowel preparation solution.

No serious adverse events were observed for the NRL994 group, but two cases of clinical significant hypokalemia in the NaP group. The number of patients having at least one related adverse event to the study medication is significantly higher in the NaP group (11.1% of patients) versus the NRL994 group (3.0%). In particular, the NaP group showed a significant number of cases with hyperphosphatemia and hypokalemia, indicating a risk for vulnerable patients who were excluded from the participation in the performed study because of the known risks associated with NaP.

In summary, NRL994 is equally effective as NaP, but provides a significant advantage of patient comfort and safety in comparison to NaP.

Conclusion:

Both the phase III trials demonstrate an efficacy of NRL994 equal to the solutions based on polyethylene glycol+electrolytes (PEG+E) or on sodium phosphate (NaP) that are often used in current clinical practice. Furthermore, NRL994 was better accepted than PEG+E, which better acceptance is related to the improved taste and lower volume to be taken. In addition, NRL994 was shown to be as safe as PEG+E in a patient group that is enhanced for risk factors (hospitalised patients). Moreover, the comparison with NaP indicated an improved safety profile for NRL994 without clinical significant electrolyte alterations or disturbances. Overall, NRL994 provides an effective and safe bowel cleansing procedure with patient compliance equivalent to that with NaP. Furthermore, NRL994 avoids the need to limit its use to younger and more healthy subjects undergoing a routine colonoscopy, as required by NaP.

What is claimed is:

1. A dry composition for admixture with water wherein the dry composition comprises, per liter of aqueous solution to be made, the following components, the components of the composition being selected such that an aqueous solution made up to 1 liter has an osmolarity within the range of from 300 to 700 mOsmol/kg:
   a) 80 to 350 g polyethylene glycol;
   b) 3 to 20 g a mixture of ascorbic acid and one or more salts of ascorbic acid;
   c) 1 to 15 g of an alkali metal or alkaline earth metal sulphate or a mixture of alkali metal or alkaline earth metal sulphates; and
   d) optionally one or more electrolytes selected from sodium chloride, potassium chloride and sodium hydrogen carbonate.

2. The dry composition as claimed in claim 1, wherein an aqueous solution made up in 1 liter of water has an osmolarity of 330 mOsmol/kg or greater.

3. The dry composition as claimed in claim 1, wherein an aqueous solution made up in 1 liter of water has an osmolarity in the range 550 mOsmol/kg or lower.

4. The dry composition as claimed in claim 1, wherein the polyethylene glycol has an average molecular weight of 2000 Daltons or greater.

5. The dry composition as claimed in claim 1, wherein the polyethylene glycol has an average molecular weight of 4500 Daltons or lower.

6. The dry composition as claimed in claim 1, wherein the polyethylene glycol has an average molecular weight of 3350 or 4000 Daltons.

7. The dry composition as claimed in claim 1, comprising from 90 g or more of polyethylene glycol per liter.

8. The dry composition as claimed in claim 1, comprising from 150 g or less of polyethylene glycol per liter.

9. The dry composition as claimed in claim 1, comprising 100 g of polyethylene glycol per liter.

10. The dry composition as claimed in claim 1, comprising the alkali metal or alkaline earth metal sulphate or the mixture of alkali metal or alkaline earth metal sulphates in a quantity of 3 g or more per liter.

11. The dry composition as claimed in claim 1, comprising the alkali metal or alkaline earth metal sulphate or the mixture of alkali metal or alkaline earth metal sulphates in a quantity 9 g or less per liter.

12. The dry composition as claimed in claim 1, comprising the alkali metal or alkaline earth metal sulphate or the mixture of alkali metal or alkaline earth metal sulphates in a quantity of 7.5 g per liter.

13. The dry composition as claimed in claim 1, wherein the alkali metal or alkaline earth metal is magnesium.

14. The dry composition as claimed in claim 1, wherein the alkali metal or alkaline earth metal is sodium.

15. The dry composition as claimed in claim 1, which comprises sodium chloride.

16. The dry composition as claimed in claim 1, comprising sodium chloride in a quantity of 2 g or more per liter.

17. The dry composition as claimed in claim 1, which comprises potassium chloride.

18. The dry composition as claimed in claim 1, comprising potassium chloride in a quantity of from 0.5 g or more per liter.

19. The dry composition as claimed in claim 1, comprising a mixture of ascorbic acid and a salt thereof in a quantity of 5 g or more per liter.

20. The dry composition as claimed in claim 1, comprising a mixture of ascorbic acid and a salt thereof in a quantity of 10 g or less per liter.

21. The dry composition as claimed in claim 1, comprising ascorbic acid and a salt thereof in a weight ratio within the range of from 1:9 to 9:1.

22. The dry composition as claimed in claim 1, comprising sodium ascorbate.

23. The dry composition as claimed in claim 1, further comprising a flavouring.

24. The dry composition as claimed in claim 1, further comprising lemon flavouring.

25. The dry composition as claimed in claim 1, further comprising a sweetener that is not a metabolic substrate for bacteria in the gut.

26. The dry composition as claimed in claim 1, further comprising a sweetener selected from the group consisting of aspartame, acesulfame K, saccharine and citric acid.

27. The dry composition as claimed in claim 1, in which the ascorbic acid and/or the salt of ascorbic acid is coated.

28. A colon cleansing preparation comprising an aqueous solution of a composition as claimed in claim 1.

29. A colon cleansing preparation sachet comprising the components of a composition as claimed in claim 1.

30. A colon cleansing composition kit comprising the components of a composition as claimed in claim 1, comprising at least two portions in which the ascorbic acid and the salts thereof are packaged in a first portion and the other components are packaged in a second portion.

31. A dry composition for admixture with water wherein the dry composition comprises, per liter of aqueous solution to be made, the following components, the components of the composition being selected such that an aqueous solution made up to 1 liter has an osmolarity within the range of from 300 to 700 mOsmol/kg: a) 30 to 350 g polyethylene glycol; b) 3 to 20 g ascorbic acid and one or more salts of ascorbic acid; and c) optionally one or more electrolytes selected from sodium chloride, potassium chloride, sodium hydrogen carbonate and the alkali metal or alkaline earth metal sulphates.

32. The dry composition as claimed in claim 31, wherein the salt of ascorbic acid is an alkali metal or alkaline earth metal ascorbate.

33. The dry composition as claimed in claim 31, wherein the salt of ascorbic acid is sodium ascorbate.

34. The dry composition as claimed in claim 31, wherein the ascorbic acid and the salt thereof are present in a weight ratio within the range of from 1:9 to 9:1.

35. The dry composition as claimed in claim 31, wherein the ascorbic acid and the salt thereof are present in a weight ratio within the range of from 4:6 to 6:4.

36. The dry composition as claimed in claim 31, wherein the composition comprises a sweetener selected from the group consisting of aspartame, acesulfame K, saccharine and citric acid.

37. The dry composition as claimed in claim 31, wherein the composition comprises sodium sulphate.

38. A colon cleansing preparation comprising an aqueous solution of a composition as claimed in claim 31.

39. A colon cleansing preparation sachet comprising the components of a composition as claimed in claim 31.

40. A colon cleansing composition kit comprising the components of a composition as claimed in claim 31, comprising at least two portions in which the ascorbic acid and the salt thereof are packaged in a first portion and the other components are packaged in a second portion.

* * * * *